US009539553B2

(12) United States Patent
Sugiyama et al.

(10) Patent No.: US 9,539,553 B2
(45) Date of Patent: Jan. 10, 2017

(54) CORONA-CORE MICROGEL EMULSIFYING AGENT AND OIL-IN-WATER EMULSIFIED COMPOSITION

(71) Applicant: Shiseido Company, Ltd., Tokyo (JP)

(72) Inventors: Yuki Sugiyama, Yokohama (JP); Tomoko Sato, Yokohama (JP); Ken Shoji, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/359,635

(22) PCT Filed: Oct. 17, 2012

(86) PCT No.: PCT/JP2012/076781
§ 371 (c)(1),
(2) Date: May 21, 2014

(87) PCT Pub. No.: WO2013/094298
PCT Pub. Date: Jun. 27, 2013

(65) Prior Publication Data
US 2014/0343170 A1    Nov. 20, 2014

(30) Foreign Application Priority Data

Dec. 22, 2011 (JP) .................. 2011-281294
Oct. 2, 2012   (JP) .................. 2012-219957

(51) Int. Cl.
A61K 8/06     (2006.01)
A61K 8/81     (2006.01)
A61Q 13/00    (2006.01)
B01F 17/00    (2006.01)
A61Q 19/00    (2006.01)
C08F 290/06   (2006.01)
C08F 220/18   (2006.01)
C11B 9/00     (2006.01)
A61K 8/91     (2006.01)
C08F 220/14   (2006.01)
C08F 220/28   (2006.01)
C08L 33/10    (2006.01)
C08L 33/12    (2006.01)
A61Q 17/04    (2006.01)

(52) U.S. Cl.
CPC .......... B01F 17/0028 (2013.01); A61K 8/062 (2013.01); A61K 8/8152 (2013.01); A61K 8/91 (2013.01); A61Q 13/00 (2013.01); A61Q 19/00 (2013.01); B01F 17/0021 (2013.01); C08F 220/14 (2013.01); C08F 220/18 (2013.01); C08F 220/28 (2013.01); C08F 290/062 (2013.01); C08L 33/10 (2013.01); C08L 33/12 (2013.01); C11B 9/00 (2013.01); A61K 2800/10 (2013.01); A61K 2800/54 (2013.01); A61K 2800/95 (2013.01); A61Q 17/04 (2013.01); A61Q 19/005 (2013.01)

(58) Field of Classification Search
None
See application file for complete search history.

(56) References Cited

U.S. PATENT DOCUMENTS

| 5,643,555 A | 7/1997 | Collin |
| 6,258,345 B1 | 7/2001 | Rouquet |
| 2002/0018789 A1 | 2/2002 | Gers-Barlag |
| 2009/0041922 A1 | 2/2009 | Kuhnle et al. |
| 2010/0135938 A1 | 6/2010 | Ishikubo et al. |

FOREIGN PATENT DOCUMENTS

| AR | WO 2004096422 A1 * | 11/2004 | ........... B01D 17/047 |
| JP | 2656226 B2 | 5/1997 | |
| JP | H11-158030 A | 6/1999 | |
| JP | 2001-518111 A | 10/2001 | |
| JP | 2005-015623 A | 1/2005 | |
| JP | 2006-036763 A | 2/2006 | |
| JP | 2006-161026 A | 6/2006 | |
| JP | 2007-106694 A | 4/2007 | |
| JP | 2007-126394 A | 5/2007 | |
| JP | 2007-238521 A | 9/2007 | |
| JP | 2007-302566 A | 11/2007 | |
| JP | 2007-302712 A | 11/2007 | |
| JP | 2007-332037 A | 12/2007 | |
| JP | 2008-291026 A | 12/2008 | |
| JP | 2009-501256 A | 1/2009 | |
| JP | 4577721 B2 | 9/2010 | |
| WO | 2006-051746 A1 | 5/2006 | |

OTHER PUBLICATIONS

Raw Machine Translation of JP2007-238521A obtained from Japan Platform for Patent Information on Jun. 3, 2015.*
Raw Machine Translation of JP2007-126394A obtained from Japan Platform for Patent Information on Jun. 3, 2015.*
Raw Machine Translation of JP2007-106694A obtained from Japan Platform for Patent Information on Jun. 3, 2015.*

(Continued)

Primary Examiner — Jessica Worsham

(57) ABSTRACT

The present invention provides a corona-core microgel emulsifying agent composed of a copolymer obtained by polymerizing polyethylene oxide macromonomers, hydrophobic monomers, and cross-linking monomers under specific conditions as well as an oil-in-water emulsified composition characteristically using said emulsifying agent for emulsification.

The object of the present invention is to provide a new corona-core microgel emulsifying agent to be used to prepare an oil-in-water emulsified composition that manifests superior emulsification stability, stability over time, and low skin irritation, and is free of stickiness at the time of application, manifests dewy freshness, is free of powdery sensation and/or squeakiness, and is superior in durability of fragrance, as well as an oil-in-water emulsified composition emulsified with said emulsifying agent.

4 Claims, 1 Drawing Sheet

(56) References Cited

OTHER PUBLICATIONS

The International Bureau of WIPO, "Notification of Transmittal of Translation of the International Preliminary Report on Patentability," issued in International Application No. PCT/JP2012/076781, of which U.S. Appl. No. 14/359,635 is a U.S. national phase entry, with a date of mailing of Jul. 3, 2014.
European Patent Office, "Extended European Search Report," issued in European Patent Application No. 12 359 980.0, which is a European counterpart of U.S. Appl. No. 14/359,635, with an issuance date of Dec. 21, 2015, 7 pages.
Isamu Kaneda and Brian Vincent, "Swelling behavior of PMMA-g-PEO microgel particles by organic solvents", Journal of Colloid and Interface Science, vol. 274, pp. 49-54 (2004), Elsevier Inc.

* cited by examiner

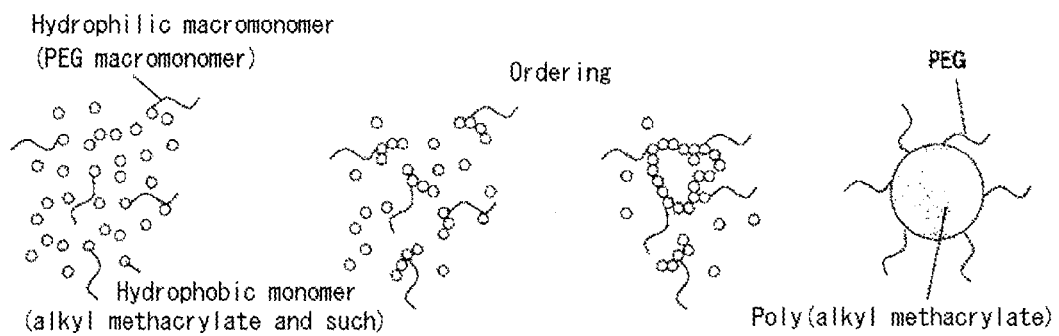

CORONA-CORE MICROGEL EMULSIFYING AGENT AND OIL-IN-WATER EMULSIFIED COMPOSITION

CROSS REFERENCE TO RELATED APPLICATIONS

This patent application is a U.S. national stage application under 35 U.S.C. §371 of International Patent Application No. PCT/JP2012/076781 filed on Oct. 17, 2012, which claims the benefit of foreign priority to Japanese Patent Application No. JP 2011-281294 filed on Dec. 22, 2011, and to Japanese Patent Application No. JP 2012-219957 filed on Oct. 2, 2012, the disclosures of all of which are hereby incorporated by reference in their entireties. The International Application was published in Japanese on Jun. 27, 2013, as International Publication No. WO 2013/094298 A1 under PCT Article 21(2).

TECHNICAL FIELD

The present invention relates to a corona-core microgel emulsifying agent and an oil-in-water emulsified composition emulsified with said emulsifying agent. More specifically, it relates to an emulsifying agent that makes it possible to prepare an oil-in-water emulsified composition that is superior in emulsification stability and texture, as well as the oil-in-water emulsified composition thereof.

BACKGROUND ART

In order to disperse liquid into another liquid, the addition of a surfactant (emulsifying agent) is usually required. An emulsifying agent has an amphiphilic molecular structure, which is composed of a polar (hydrophilic) molecular part and a nonpolar (hydrophobic) molecular part, which are spatially separated from each other.

Oil-in-water emulsions used in cosmetics and such stably mix the water-based ingredients and oil-based ingredients using the emulsifying action of the added surfactant. That is, finely dispersed liquid drops of the oil phase are surrounded by shells of the emulsifying agent and the outer phase is the water phase that is the continuous phase; this is said to be the reason for superior texture that gives a dewy fresh tactile sensation.

On the other hand, with the increase in the number of consumers who attach more importance to safety, some of the very sensitive users demand an oil-in-water emulsion that does not have a surfactant that might give irritation or has it in a low enough content to avoid such irritation.

An emulsion prepared by adsorbing powder to the interface, without using a surfactant, is conventionally known as Pickering emulsion.

In the early 1900s, Pickering prepared paraffin/water emulsions that were stabilized by simply adding a colloidal solid such as basic copper sulfate, basic iron sulfate, or metal salts of sulfuric acid. Therefore, this type of emulsion is called a Pickering emulsion. Pickering disclosed the following conditions for the stability of this type of emulsion. (1) The solid particles are suitable for stabilization only when they are significantly smaller than the liquid drops in the inner phase and they don't have a tendency to form aggregates. (2) One of the important properties of the emulsion stabilizing colloidal solid is its wettability. For an O/W emulsion to be stabilized, the colloidal solid is not necessarily more wettable with water than, for example, oil.

Pickering emulsions originally surfaced as unwanted secondary effects in a multitude of situations in industrial processes such as the secondary recovery of petroleum, Bitumen extraction from tar sand, and other separation processes involving two types of non-mixing fluids and fine dispersed solid particles. Therefore, the investigation of the corresponding system such as oil/water/soot or oil/water/slate dust system was the original focus of the research.

Pickering emulsions can be seen in various natural and industrial processes such as crude oil recovery, oil separation, cosmetics, and wastewater treatment.

Many research results have been reported on the preparation of Pickering emulsions (Non-Patent Document 1, for example), and its utilization has been proposed in the perfumery and cosmetics field as well (Patent Documents 1-3).

However, preparation of an oil-in-water Pickering emulsion that can satisfy temperature stability and stirring stability in various environments, which is essential when applying emulsions for perfumery and cosmetics, has been very difficult. For example, in the case of an oil-in-water Pickering emulsion as described above, powder normally is adsorbed on the interface and stably disperses emulsified particles in the emulsion but, when the emulsion is stirred as it is transported and such, the emulsified particles collide with each other and temporarily transform to expose the interface on which the powder is not adsorbed. The exposed interfaces sometimes coalesce to cause aggregation. Therefore, in terms of emulsification stability, conventional oil-in-water Pickering emulsions can hardly be said to be usable as products such as cosmetics.

Recently it has been reported that a stable oil-in-water emulsified composition can be obtained by the combined use of a specific cationic surfactant, polyhydric alcohol, and powder to emulsify the oil phase containing an amphiphilic lipid such as ceramide (see Patent Document 4).

However, Patent Document 4 requires an amphiphilic substance, which forms a liquid crystal structure (a gel) with the surfactant to stabilize the system, but there is a tendency for stickiness at the time of use. Technology to add a very small amount of an amphiphilic substance has been reported (Non-Patent Document 2, for example), but it is difficult to obtain what is sufficiently stable for perfumery and cosmetics; also a new problem arises in terms of the texture during use such as stickiness of the product due to the amphiphilic substance.

Also, Patent Document 5 reports that an oil-in-water emulsion that has superior emulsification stability, is free of stickiness and low in irritation can be obtained by adding specific amounts of powder, oil phase ingredients, water phase ingredients, and a cationic surfactant containing two-chain alkyls. In the invention described in Patent Document 5, it is discovered that, by incorporating the cationic surfactant treatment of the powder into the preparation process of the oil-in-water emulsion, said oil-in-water emulsified composition can easily be obtained.

However, the powder used as the emulsifying agent in these Pickering emulsions is mainly inorganic powder (Patent Document 1: polyalkylsilsesquioxane particles, Patent Document 2: metal oxide, Patent Document 3: silica/titanium dioxide/zinc oxide, Patent Document 4: inorganic powder and such, Patent Document 5: hydrophobized fine particle titanium dioxide, red iron oxide, yellow iron oxide, black iron oxide, and aluminum oxide) and the emulsifying ability of these powders is inferior to that of surfactants, therefore the blend ratio has to be higher than that for conventional surfactants.

As a result, squeakiness and powdery sensation from the use of powder and whiteness after the application cannot be avoided, and therefore most of them are inferior in terms of texture during use.

Patent Document 6 reports Pickering emulsions using spherical organic particles as the emulsifying agent; but the required blend ratio, combined with elastomer-like organopolysiloxane, is 10% or more and the powdery sensation is not quite reduced.

Patent Document 7 reports that a hydrophobic monomer emulsion (Pickering emulsion) can be obtained by using hydrophobin as the emulsifying agent. Non-Patent Document 3 reports that a Pickering emulsion can be obtained by using a flavonoid as the emulsifying agent. However, the use of flavonoids and proteins such as hydrophobin raises the concern of allergies and such, and therefore there are many problems in external preparation applications.

Methods for preparing a corona-core microgel are reported in Patent Document 8, Non-Patent Document 4 and such. Patent Document 9 describes cosmetics into which a corona-core microgel is blended. However, Patent Document 9 proposes the corona-core microgel be a white turbidity agent for providing a white turbid cosmetic. Most of Examples are cosmetics having water-based base agents such as lotions and essences; the corona-core microgel is not used as an emulsifying agent; using a corona-core microgel as the emulsifying agent to prepare an oil-in-water emulsified composition is new. And, in the present invention, a corona-core microgel was found to function as an emulsifying agent, and an oil-in-water emulsified composition superior in stability and texture obtained by using said emulsifying agent is a new invention.

PRIOR ART DOCUMENTS

Patent Documents

Patent Document 1: Japanese Patent No. 2656226
Patent Document 2: JP 2001-518111 A
Patent Document 3: JP 2007-332037 A
Patent Document 4: JP 2006-36763 A
Patent Document 5: JP 2008-291026 A
Patent Document 6: JP H11-158030 A
Patent Document 7: JP 2009-501256 A
Patent Document 8: JP 2006-161026 A
Patent Document 9: Japanese Patent No. 4577721

Non-Patent Documents

Non-Patent Document 1: B. Binks et. al, Advances in Colloid and Interface Science, 100-102 (2003) Non-Patent Document 2: Mukul M, Sharma et. al, Journal of Colloid and Interface Science, 157, 244-253 (1993).
Non-Patent Document 3: J. Agric. Food Chem., 59, 263-2645 (2011).
Non-Patent Document 4: J. Colloid Interface Sci., 274, 49 (2004).

DISCLOSURE OF INVENTION

Technical Problem

The present invention was carried out in view of the aforementioned situation and its object is to develop a new emulsifying agent and provide an oil-in-water emulsified composition that is superior in emulsification stability, low in skin irritation, superior in dewy freshness, and low in squeakiness and powdery sensation.

Technical Solution

That is, the present invention provides a corona-core microgel emulsifying agent composed of a copolymer characteristically obtained by polymerizing polyethylene oxide macromonomers of the following formula (1), hydrophobic monomers of the following formula (2), and cross-linking monomers of the following formula (3) under the following conditions (A) and (B).

(A) The mole ratio of the feed mole amount of said polyethylene oxide/feed mole amount of the hydrophobic monomers is 1:10-1:250.

(B) The feed amount of said cross-linking monomers is 0.1-1.5 wt % relative to the feed amount of said hydrophobic monomers.

[Chemical formula 1]

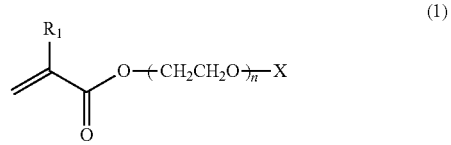

(1)

$R_1$ denotes an alkyl having 1-3 carbon atoms, and n is an integer 8-200. X denotes H or $CH_3$.

[Chemical formula 2]

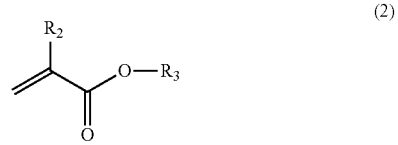

(2)

$R_2$ denotes an alkyl having 1-3 carbon atoms, and $R_3$ denotes an alkyl having 1-12 carbon atoms.

[Chemical formula 3]

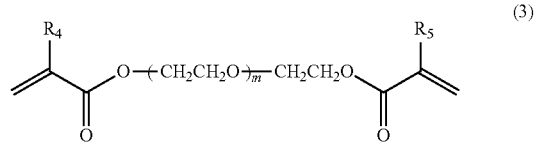

(3)

$R_4$ and $R_5$ each independently denote an alkyl having 1-3 carbon atoms, and m is a number 0-2.

Also, the present invention provides the aforementioned corona-core microgel emulsifying agent wherein the following conditions (C) and (D) are added for radical polymerization of polyethylene oxide macromonomers of the following formula (1), hydrophobic monomers of the following formula (2), and cross-linking monomers of the following formula (3) in a water-ethanol mixed solvent to obtain the copolymer constituting the aforementioned corona-core microgel emulsifying agent.

(C) The hydrophobic monomers of the following formula (2) have a monomer composition of a mixture of one, two, or more methacrylic acid derivatives that have an alkyl having 1-8 carbon atoms.

(D) The water-ethanol mixed solvent has a volume ratio at 20° C. of water:ethanol=90-30:10-70.

[Chemical formula 4]

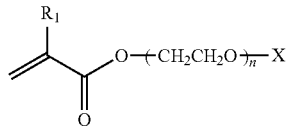

(1)

$R_1$ denotes an alkyl having 1-3 carbon atoms, and n is an integer 8-200. X denotes H or $CH_3$.

[Chemical formula 5]

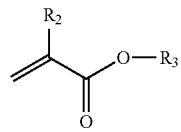

(2)

$R_2$ denotes an alkyl having 1-3 carbon atoms, and $R_3$ denotes an alkyl having 1-12 carbon atoms.

[Chemical formula 6]

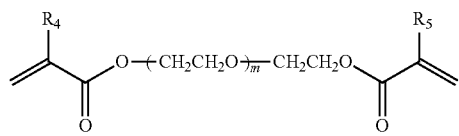

(3)

$R_4$ and $R_5$ each independently denote an alkyl having 1-3 carbon atoms, and m is a number 0-2.

Furthermore, the present invention provides an oil-in-water emulsified composition comprising the aforementioned (a) corona-core microgel emulsifying agent, (b) oil phase ingredients, and (c) water phase ingredients.

Also, the present invention provides the aforementioned oil-in-water emulsified composition characteristically comprising perfume as (b) oil phase ingredient.

Advantageous Effects of the Invention

By utilizing the present invention, a corona-core microgel emulsifying agent and an oil-in-water emulsified composition that are superior in emulsifying properties, emulsification stability, and texture can easily be obtained.

(1) The corona-core microgel emulsifying agent of the present invention and an oil-in-water emulsified composition using said emulsifying agent have superior emulsification properties. Even if the blend ratio of the corona-core microgel emulsifying agent is small, good oil-in-water emulsified compositions can be obtained. Also, even if the ratio of the oil phase ingredients/water phase ingredients is high (the amount of the oil phase ingredients is large), a good oil-in-water emulsified composition can be obtained.

(2) The corona-core microgel emulsifying agent of the present invention and an oil-in-water emulsified composition using said emulsifying agent have superior emulsification stability. Unlike conventional Pickering emulsions, the emulsified state is not damaged by stirring or vibration, and the temperature stability is also good because there is little change in the physical properties of the surfactant due to temperature just like emulsions obtained by using a conventional surfactant.

(3) An oil-in-water emulsified composition using the corona-core microgel emulsifying agent of the present invention has superior texture. Squeakiness and powdery sensation due to the use of powder, which is seen with conventional Pickering emulsions, are reduced and there is no stickiness due to the surfactant, which is seen with emulsions obtained by using a conventional surfactant, resulting in superior dewy freshness. Also, the oil-in-water emulsified composition of the present invention has suppressed skin irritability as well. Furthermore, when a perfume is blended in as an oil phase ingredient, an oil-in-water emulsified composition having a superior durability of fragrance can be provided.

BRIEF DESCRIPTION OF DRAWINGS

FIG. 1 is an illustration showing the mechanism of generation of the corona-core microgel emulsifying agent of the present invention.

BEST MODE FOR CARRYING OUT THE INVENTION

Embodiments of the present invention is described in detail below.

"Regarding the copolymer that constitutes (a) the corona-core microgel emulsifying agent of the present invention"

The corona-core microgel emulsifying agent of the present invention is a microgel composed of a copolymer obtained by polymerizing monomers represented by formulas (1)-(3). Methods for preparing a microgel composed of said copolymer are reported in Patent Document 8, Non-Patent Document 4 and such.

For the polyethylene oxide macromonomers of formula (1), reagents commercially available from Aldrich or BLEMMER (registered trademark) sold by NOF Corporation can be used.

The molecular weight (i.e. the value of n) of the polyethylene oxide part of formula (1) used in the present invention is in the range of n=8–200. Preferable examples include BLEMMER (registered trademark) PME-400, BLEMMER (registered trademark) PME-1000, and BLEMMER (registered trademark) PME-4000 from NOF Corporation.

[Chemical formula 1]

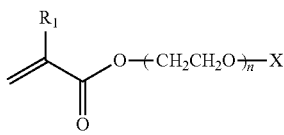

(1)

$R_1$ denotes an alkyl having 1-3 carbon atoms, and n is an integer 8-200. X denotes H or $CH_3$.

For the hydrophobic monomer of formula (2), reagents are commercially available from Aldrich or Tokyo Chemical Industry Co., Ltd. For the alkyl chain of $R_3$ of formula (2), alkyls having 1-8 carbon atoms are even more preferable.

[Chemical formula 2]

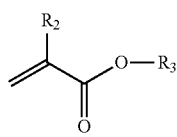

(2)

R₂ denotes an alkyl having 1-3 carbon atoms, and R₃ denotes an alkyl having 1-12 carbon atoms.

Specific examples of formula (2) include methyl acrylate, ethyl acrylate, propyl acrylate, butyl acrylate, pentyl acrylate, hexyl acrylate, heptyl acrylate, octyl acrylate, decyl acrylate, dodecyl acrylate, methyl methacrylate, ethyl methacrylate, propyl methacrylate, butyl methacrylate, pentyl methacrylate, hexyl methacrylate, heptyl methacrylate, octyl methacrylate, decyl methacrylate, and dodecyl methacrylate. Particularly preferable are methyl methacrylate, butyl methacrylate, and octyl methacrylate.

These hydrophobic monomers are commodity raw materials and they can also be obtained easily as general industrial raw materials.

The cross-linking monomer of formula (3) can be obtained as a commercially available reagent or an industrial raw material. This cross-linking monomer is preferably hydrophobic.

A preferable value range of m in formula (3) is 0-2. Specific preferable examples include ethylene glycol dimethacrylate (hereafter sometimes abbreviated as EGDMA) sold by Aldrich and BLEMMER and PDE-50 (registered trademark) from NOE Corporation.

[Chemical formula 3]

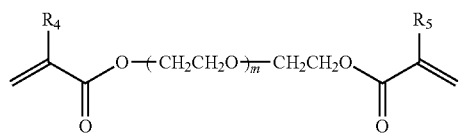

(3)

R₄ and R₅ each independently denote an alkyl having 1-3 carbon atoms, and m is a number 0-2.

The copolymer that constitutes the corona-core microgel used in the present invention is prepared by copolymerizing the aforementioned monomers under the following conditions (A) and (B) with any polymerization method.

(A) The mole ratio of the feed mole amount of said polyethylene oxide/feed mole amount of the hydrophobic monomers is 1:10-1:250.

(B) The feed amount of said cross-linking monomers is 0.1-1.5 wt % relative to the feed amount of said hydrophobic monomers.

In the present invention, "the feed amount of said cross-linking monomer over the feed amount of said hydrophobic monomer" is defined as the cross-link density (wt %). Due to condition (B), the cross-link density of the copolymer (microgel) used in the present invention, as defined as the feed amount of said cross-linking monomers relative to the feed amount of said hydrophobic monomers, must be 0.1-1.5 wt %.

In the present invention, a copolymer (microgel) obtained by adding the following conditions (C) and (D) in addition to the aforementioned conditions (A) and (B) and conducting radical polymerization of the monomers of formulas (1)-(3) in a water-ethanol mixed solvent is preferable.

(C) The hydrophobic monomers of the following formula (2) have a monomer composition of a mixture of one, two, or more methacrylic acid derivatives that have an alkyl having 1-8 carbon atoms.

(D) The water-ethanol mixed solvent has a volume ratio at 20° C. of water:ethanol=90-30 10-70.

For the mole quantity of the polyethylene oxide macromonomer and the hydrophobic monomer, a corona-core microgel can be polymerized when the mole ratio of the feed mole amount of said polyethylene oxide/feed mole amount of the hydrophobic monomers is in the range of 1:10-1:250 (mole ratio) as specified in condition (A).

If the feed amount of the polyethylene oxide macromonomer is less than a tenth of that of the hydrophobic monomer in the mole ratio, the polymerized polymer becomes water soluble and does not form a corona-core microgel. Also, if the mole amount of the hydrophobic monomer is 250 times or more of that of the polyethylene oxide macromonomer, then the dispersion stabilization by the polyethylene oxide macromonomer becomes deficient and the hydrophobic polymer forms insoluble hydrophobic monomer aggregates and precipitates. The feed mole ratio of the polyethylene oxide macromonomer and the hydrophobic monomer is preferably in the range of 1:10 to 1:200. More preferably it is in the range of 1:25 to 1:100.

By copolymerizing with the cross-linking monomer according to condition (B), a microgel whose core part has a cross-linked hydrophobic polymer can be polymerized.

If the feed amount of the cross-linking monomer is less than 0.1 wt % relative to the feed amount of the hydrophobic monomer, then the cross-link density is low and this microgel breaks down when swollen. If it is over 1.5 wt %, then aggregation of microgel particles occurs and it is impossible to polymerize preferable microgel particles having a narrow particle size distribution. The feed amount of the cross-linking monomer is preferably 0.2-1.0 wt %, more preferably 0.2-0.8 wt %, most preferably 0.2-0.5 wt %.

In the present invention, the hydrophobic monomers of formula (2) preferably have a monomer composition of a mixture of one, two, or more methacrylic acid derivatives that have an alkyl having 1-8 carbon atoms, which is condition (C). When the number of carbon atoms is 0 (when the monomer does not have an end ester bond), the monomers may be too hydrophilic for good emulsification polymerization. On the other hand, if the number of carbon atoms is 9 or more, then steric hindrance occurs during the polymerization and the cross-linking structure may not be formed well.

Condition (D) dictates that the mix ratio of the water/ethanol, which is the polymerization solvent, be water:ethanol=90-30:10-70 (volume ratio at 20° C.).

For the polymerization solvent, it is preferable to add ethanol for homogeneous dissolution of the hydrophobic monomer. The mix ratio of ethanol is 10-70 volume ratio. When the mix ratio of ethanol is lower than a volume ratio of 10, then it becomes difficult to solubilize the hydrophobic monomer and the particle size distribution of the polymerized microgel particles becomes wide. Also, if the mix ratio of ethanol is over a volume ratio of 70, then the polymerized polymer is dissolved in the solvent and microgel particles cannot be obtained.

A more preferable mix ratio of the water/ethanol in the water-ethanol mixed solvent is water:ethanol=90-60:10-40 (volume ratio at 20° C.). Particularly preferable is water:ethanol=80-70:20-30 (volume ratio at 20° C.).

For the polymerization initiator for use in this polymerization system, commercially available polymerization initiators used for water soluble thermal radical polymerization can be used. With this polymerization system, polymerized microgel particles having a very narrow particle size distribution can be obtained without accurately controlling the stirring conditions.

Microgels from conventional synthetic polymers all use polymer electrolytes, polyacrylic acid for example, whose dispersibility in water lacks acid resistance and/or salt resistance. However, when considering applications as ingredients for medical drugs and/or cosmetics, acid resistance and/or salt resistance are very important features to adapt to physiological conditions. The aforementioned microgel of the present invention is a microgel stabilized by polyethylene oxide chains, which are a nonionic polymer, and its dispersion stability in water can be expected to have acid resistance and/or salt resistance.

The polymer fine particle polymerization method by the macromonomer method using macromonomers containing a water soluble polymer structure is known, but a method that uses this method to cross-link the core part with cross-linking monomers to prepare a microgel is not known.

In the microgel used in the present invention, it is believed that the hydrophilic macromonomer and the hydrophobic monomer are ordered in the solvent as shown in FIG. 1 and a corona-core microgel having an almost constant particle size and a cross-linked core part is generated.

And it is believed that this corona-core microgel functions as a superior Pickering emulsion emulsifying agent.

The copolymer used for the corona-core microgel emulsifying agent was described thus far. Conventionally the corona-core microgel has not been used as an emulsifying agent and the present invention is a use invention of the corona-core microgel as an emulsifying agent.

The corona-core microgel emulsifying agent of the present invention emulsifies the oil phase ingredients and the water phase ingredients to form an oil-in-water emulsified composition having a structure in which the corona-core microgel emulsifying agent is adsorbed onto the oil drops of the oil phase ingredients dispersed in the water phase ingredients. Therefore, the corona-core microgel emulsifying agent of the present invention has a superior emulsifying ability and, by using the corona-core microgel emulsifying agent as the emulsifying agent, an oil-in-water emulsified composition having exceptional emulsification stability can be prepared.

The oil-in-water emulsified composition of the present invention is prepared by mixing and dispersing a corona-core microgel emulsifying agent composed of said copolymer in water or the water phase ingredients, adding the oil phase ingredients and other ingredients, and emulsifying the mixture by stirring and applying shearing force.

That is, the oil-in-water emulsified composition of the present invention has a superior commercial value in that it can be produced with a very easy preparation method.

The blend ratio of the corona-core microgel emulsifying agent used as the emulsifying agent in the present invention is usually 0.01-10 wt %, preferably 0.1-10 wt %, relative to the total amount of the oil-in-water emulsified composition.

If the blend ratio of the microgel is less than 0.01 wt %, then it is difficult to obtain a stable oil-in-water emulsified composition; and if the blend ratio is over 10 wt %, then it may not be preferable as a cosmetic in terms of stability during long term storage at high temperatures and the texture may not be desirable.

"(b) Regarding the oil phase ingredients used in the oil-in-water emulsified composition of the present invention"

Examples of the oil phase ingredients contained in the oil-in-water emulsified composition of the present invention include hydrocarbon oils, higher fatty acids, higher alcohols, synthetic esters, silicone oils, liquid fats and oils, solid fats and oils, and waxes that are commonly used in cosmetics, quasi-drugs, etc.; one, two, or more oil-based ingredients can be used.

There is no particular limitation for the oil phase ingredients; a preferable blend ratio is 5-90 wt %, more preferably 10-80 wt %, relative to the total amount of the oil-in-water emulsified composition.

Examples of the hydrocarbon oils include isododecane, isohexadecane, isoparaffin, liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain alcohols (for example, monostearyl glycerin ether (batyl alcohol), 2-decyltetradecynol, lanolin alcohol, cholesterol, phytosterol, hexyl dodecanol, isostearyl alcohol, and octyl dodecanol).

Examples of the synthetic ester oils include octyl octanoate, nonyl nonanoate, cetyl octanoate, isopropyl myristate, octyl dodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, n-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, pentaerythritol tetra-2-ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, castor oil fatty acid methyl ester, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane), ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, various modified polysiloxanes (amino-modified polysiloxane, polyether-modified polysiloxane, alkyl-modified polysiloxane, and fluorine-modified polysiloxane), and acryl silicones.

Examples of the liquid fats and oils include avocado oil, tsubaki oil, turtle fatty acid, macademia nut oil, corn oil, mink oil, olive oil, rapeseed oil, egg yolk oil, sesame oil, persic oil, wheat germ oil, sasanquan oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerin.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Furthermore, by using perfume as (b) the oil phase ingredient of the present invention, an oil-in-water emulsified composition having a superior durability of fragrance can be obtained. Selection of the perfume used in the present invention is not limited in particular; examples include natural perfumes from animals or plants, synthetic perfumes prepared by means of chemical synthesis, and perfume blends thereof. In the present invention, any one, two, or more of these perfumes can be used as appropriate for the target product. For the perfume ingredients, one, two or more selected from the following can be used: acetivenol, anise aldehyde, anethole, amyl acetate, amyl salicylate, allyl amyl glycolate, allyl caproate, aldehyde C6-20, ambrettolide, ambrettolide, ambroxan, ionone, Iso E Super, eugenol, auranthiol, galaxolide, calone, coumarin, geraniol, geranyl acetate, Sandalore, santalol, sandela, cyclamen aldehyde, cis-3-hexenyl acetate, cis-3-hexenol, citral, citronellyl acetate, citronellol, cineole, dihydromyrcenol, jasmolactone, cinnamic alcohol, cinnamic aldehyde, styralyll acetate, cedryl acetate, cedrol, damascone, damascenone, decalactone, terpinyl acetate, terpineol, tonalid, tonalide, triplal, nerol, bacdanol, vanillin, hydroxycitronellal, phenylethyl acetate, phenylethyl alcohol, hexyl salicylate, vetiveryl acetate, hedione, heliotropin, helional, vertofix, benzyl acetate, benzyl salicylate, benzyl benzoate, pentalide, pentalide, bornyl acetate, myol, musk ketone, methyl anthranilate, methyl dihydrojasmonate, yara yara, lime oxide, linalyl acetate, linarol, limonene, Lyral, lilial, rose oxide, rhodinol, *Angelica* oil, anise oil, *Artemisia vulgaris* oil, basil oil, bay oil, Bergamot oil, calamus oil, camphor oil, cananga oil, cardamom oil, *cassia* oil, cedar wood oil, celery oil, chamomile oil, cinnamon oil, clove oil, coriander oil, cumin oil, dill oil, elemi oil, estragon oil, eucalyptus oil, fennel oil, fenugreek oil, *galbanum* oil, geranium oil, ginger oil, grapefruit oil, gaiac wood oil, cypress leaf oil, cypress oil, juniper berry oil, lavandin oil, lavender oil, lemon oil, lime oil, mandarin oil, ziram oil, mimosa oil, peppermint oil, spearmint oil, mill oil, myrtle oil, nutmeg oil, oakmoss oil, olibanum oil, opoponax oil, orange oil, parsley oil, patchouli oil, pepper oil, perilla oil, petit grain oil, neroli oil, orange flower, oil, pimento oil, all spice oil, pine oil, rose oil, rosemary oil, clary sage oil, sage oil, sandalwood oil, styrax oil, taget oil, thyme oil, tuberose oil, valerian oil, vetiver oil, violet leaf oil, wintergreen oil, wormwood oil, ilan ilan oil, yuzu oil, cassie absolute, genet absolute, hyacinth absolute, immortelle absolute, jasmine absolute, jonquil absolute, narcis absolute, rose absolute, violet leaf absolute, and benzoin.

The blend ratio of the perfume is usually 0.5-40 wt %, preferably 1-30 wt %, and more preferably 2-20 wt %, of the total amount of the oil-in-water emulsified composition. If it is less than 0.5 wt %, then a sufficient level and duration of the fragrance cannot be obtained, which is not preferable.

In the case of conventional emulsified compositions obtained by surfactants, the physical properties of the surfactant and the physical properties of the oil component significantly influence emulsifiability, and changes in the oil component required changes in the types of the surfactant.

However, since the oil-in-water emulsified composition of the present invention is a Pickering emulsion using a corona-core microgel for the emulsifying agent, the type of the oil component does not greatly influence emulsifiability, stability and such and therefore a wider range of types of the oil component can be blended in.

"(c)) Regarding the water phase ingredients used in the oil-in-water emulsified composition of the present invention"

Water, water soluble alcohols, thickeners, etc. commonly used in cosmetics, quasi-drugs, etc. can be blended into the water phase of the oil-in-water emulsified composition of the present invention; in addition, appropriate amounts of humectants, chelating agents, preservatives, pigments, etc. can also be blended in as desired.

There is no particular limitation for the water phase ingredients; a preferable blend ratio is 10-95 wt %, more preferably 20-90 wt %, relative to the total amount of the oil-in-water emulsified composition.

Also, in the oil-in-water emulsified composition of the present invention, a preferable mass ratio of the oil phase and the water phase is oil phase:water phase=10:90-80:20.

The selection of water contained in the oil-in-water emulsified composition of the present invention is not limited in particular; specific examples include purified water, ion-exchanged water, and tap water.

The water soluble alcohol is one, two, or more selected from lower alcohols, polyhydric alcohols, polyhydric alcohol polymers, dihydric alcohol alkyl ethers, dihydric alcohol ether esters, glycerin monoalkyl ethers, sugar alcohols, monosaccharides, oligosaccharides, polysaccharides, and derivatives thereof.

Examples of the lower alcohols include ethanol, propanol, isopropanol, isobutyl alcohol, and t-butyl alcohol.

Examples of the polyhydric alcohols include: dihydric alcohols (for example, dipropylene glycol, 1,3-butylene glycol, ethylene glycol, trimethylene glycol, 1,2-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, diglycerin and pentaerythritol such as 1,2,6-hexanetriol); pentahydric alcohols (for example, xylitol and triglycerin); hexahydric alcohols (for example, sorbitol and mannitol); polyhydric alcohol polymers (for example, diethylene glycol, dipropylene glycol, triethylene glycol, polypropylene glycol, tetraethylene glycol, diglycerin, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin mono alkyl ethers (for example, xylyl alcohol, selachyl alcohol, and batyl alcohol); sugar alcohols (for example, maltotriose, mannitol, sucrose, erythritol, glucose, fructose, starch amylolysis sugar, maltose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether; POP-glycerin ether phosphoric acid; POP/POE-pentane erythritol ether; and polyglycerin.

Examples of the monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, gentianose, umbelliferose, lactose, planteose, isolignoses, α,α-trehalose, raffinose, lignoses, umbilicine, stachyose and verbascoses.

Examples of polysaccharides include cellulose, quince seed, starch, galactan, dermatan sulfate, glycogen, gum arabic, heparan sulfate, traganth gum, keratan sulfate, chondroitin, xanthan gum, guar gum, dextran, kerato sulfate, locust bean gum, and succinoglucan.

Examples of the polyol include polyoxyethylene methyl glucoside (Glucam E-10) and polyoxypropylene methyl glucoside (Glucam P-10).

Examples of the thickeners include: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the natural water-soluble polymer include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (for example, sodium alginate and propylene glycol alginate).

Examples of the synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, polyethylene glycol 20,000, 40,000, 60,000, etc.); acrylic polymers (for example, sodium polyacrylate, polyethylacrylate, and polyacrylamide); polyethyleneimine; and cationic polymers.

Examples of the humectant include chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of the sequestering agents include 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, and glutathione.

Examples of the pH adjustment agents include buffers such as lactic acid-sodium lactate, citric acid-sodium citrate, and succinic acid-sodium succinate.

The blend ratios of the oil phase ingredients and the water phase ingredients in the oil-in-water emulsified composition of the present invention are not prescribed in particular. By using the microgel of (a), an oil-in-water emulsified composition with a wide range of oil phase ingredients/water phase ingredients ratios, ranging from embodiments having smaller oil phase ingredients/water phase ingredients ratios, i.e., smaller blend ratios of the oil phase ingredients (essences, emulsions, etc.) to embodiments having larger blend ratios of the oil phase ingredients (cleansing creams, sunscreens, hair creams, etc.) can be obtained.

Other ingredients normally used in external preparations such as cosmetics and quasi-drugs can be blended as necessary in the oil-in-water emulsified composition of the present invention as long as the effect of the present invention is not adversely affected; examples of such ingredients include ultraviolet absorbents, powders, organic amines, polymer emulsions, vitamins, and antioxidants.

Examples of the water soluble ultraviolet absorbent include benzophenone-type ultraviolet absorbents such as 2,4-dihydroxybenzophenone, 2,2'-dihydroxy-4-methoxy benzophenone, 2,2'-dihydroxy-4,4'-dimethoxybenzophenone, 2,2',4,4'-tetrahydroxy benzophenone, 2-hydroxy-4-methoxy benzophenone, 2-hydroxy-4-methoxy-4'-methyl-benzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone, and 4-hydroxy-3-carboxy benzophenone, the benzimidazole-type ultraviolet absorbent such as phenylbenzimidazole-5-sulfonic acid and salts thereof and phenylene-bis-benzimidazole-tetrasulfonic acid and salts thereof, as well as 3-(4'-methylbenzylidene)-d,l-camphor, 3-benzylidene-d,l-camphor, urocanic acid, and urocanic acid ethyl ester.

Examples of the oil soluble ultraviolet absorbent include the following: benzoic acid-type ultraviolet light absorbents such as paraminobenzoic acid (PABA), PABA monoglycerin ester, N, N-dipropoxy PABA ethyl ester, N, N-diethoxy PABA ethyl ester, N,N-dimethyl PABA ethyl ester, and N, N-dimethyl PABA butyl ester; anthranilic acid-type ultraviolet light absorbents such as homo mentyl-N-acetyl anthranilate; salicylic acid-type ultraviolet light absorbents such as amyl salicylate, mentyl salicylate, homo mentyl salicylate, octyl salicylate, phenyl salicylate, benzyl salicylate, and p-isopropanol phenyl salicylate; cinnamic acid-type ultraviolet absorbents such as octyl cinnamate, ethyl-4-isopropyl cinnamate, methyl-2,5-diisopropyl cinnamate, ethyl-2,4-diisopropyl cinnamate, methyl-2,4-di isopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethyl hexanoyl-diparamethoxy cinnamate, and 3-methyl-4-[methylbis(trimethylsilixy)silyl]butyl 3,4,5-trimethoxy cinnamate; 2-phenyl-5-methyl benzoxazole, 2,2'-hydroxy-5-methylphenyl benzotriazol, 2-(2'-hydroxy-5'-t-octylphenyl) benzotriazol, 2-(2'-hydroxy-5'-methylphenyl)benzotriazol, dibenzaladine, dianisoylmethane, 4-methoxy-4'-t-butyl dibenzoyl-methane, and 5-(3,3'-dimethyl-2-norbornylidene)-3-pentane-2-one, and octocrylene.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, zinc myristate, calcium palmitate, and aluminum stearate), and boron nitride); organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, mango violet, cobalt violet); inorganic green pigments (for example, chromium oxide, chromium hydroxide, and cobalt titanate); inorganic blue pigments (for example, ultramarine blue and Berlin blue); pearl pigment (for example, titanium oxide coated mica, titanium oxide coated bismuth oxychloride, titanium oxide coated talc, coloration titanium oxide coated mica, bismuth oxychloride, fish scale flakes); metal powder pigments (for example, aluminum powder, copper powder); organic pigments such as zirconium, barium or aluminum rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1); and natural colors (for example, chlorophyll and β-carotene).

Examples of the organic amines include monoethanolamine, diethanolamine, triethanolamine, morpholine, tetrakis(2-hydroxypropyl)ethylenediamine, triisopropanolamine, 2-amino-2-methyl-1,3-propanediol, and 2-amino-2-methyl-1-propanol.

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of vitamins include vitamins A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic acid ester.

Examples of antioxidation assistants include phosphoric acid, citric acid, ascorbic acid, maleic acid, malonic acid, succinic acid, fumaric acid, cephalin, hexametaphosphate, phytic acid, and ethylene diamine tetraacetic acid.

Examples of other possible ingredients include antiseptics (methylparaben, ethylparaben, butylparaben, and phenoxyethanol); antiphlogistic agents (for example, glycyrrhizic acid derivatives, glycyrrhetinic acid derivatives, salicylic acid derivatives, hinokitiol, zinc oxide, and allantoin); whitening agents (for example, placenta extract, creeping saxifrage extract, and arbutin); various extracts (for example, Phellodendri Cortex, goldthread, lithospermum root, *Paeonia lactiflora, Swertia japonica*, Birch, sage, loquat, carrot, aloe, *Malva sylvestris*, Iris, grape, *Coix* ma-yuen, sponge gourd, lily, saffron, *Cnidium officinale*, sheng jiang, *Hypericum erectum*, Ononis, garlic, Guinea pepper, chen pi, *Ligusticum acutilobum*, and seaweed), activators (royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); anti-seborrhea agents (for example, sulfur and thiantol); and anti-inflammatory agents (for example, tranexamic acid, thiotaurine, and hypotaurine).

Also, not as the emulsifying agent but for the purpose of controlling tactile sensations during use, controlling drug permeation and such, or improving washability when blended into washing agents for skin and hair, surfactants can be blended into the water phase or oil phase of the oil-in-water emulsified composition of the present invention.

An ampholytic surfactant has at least one cationic functional group and one anionic functional group, is cationic when the solution is acidic and anionic when the solution is alkaline, and assumes characteristics similar to a nonionic surfactant around the isoelectric point.

Ampholytic surfactants are classified, based on the type of the anionic group, into the carboxylic acid type, the sulfuric ester type, the sulfonic acid type, and the phosphoric ester type. For the present invention, the carboxylic acid type, the sulfuric ester type, and the sulfonic acid type are preferable. The carboxylic acid type is further classified into the amino acid type and the betaine type. Particularly preferable is the betaine type.

Specific examples include: imidazoline type ampholytic surfactants (for example, 2-undecyl-N,N,N-(hydroxyethyl carboxymethyl)-2-imidazoline sodium salt and 2-cocoyl-2-imidazolinium hydroxide-1-carboxyethyloxy 2 sodium salt); and betaine type surfactants (for example, 2-heptadecyl-N-carboxymethyl-N-hydroxyethyl imidazolinium betaine, lauryldimethylaminoacetic acid betaine, alkyl betaine, amide betaine, and sulfobetaine).

Examples of the cationic surfactant include quaternary ammonium salts such as cetyltrimethylammonium chloride, stearyltrimethylammonium chloride, behenyltrimehylammonium chloride, behenyldimethylhydroxyethylammonium chloride, stearyldimethylbenzylammonium chloride, and cetyltrimethylammonium methyl sulfate. Other examples include amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic di ethylaminopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Anionic surfactants are classified into the carboxylate type such as fatty acid soaps, N-acyl glutamates, and alkyl ether acetates, the sulfonic acid type such as α-olefin sulfonates, alkane sulfonates, and alkylbenzene sulfonates, the sulfuric ester type such as higher alcohol sulfuric ester salts, and phosphoric ester salts. Preferable are the carboxylate type, the sulfonic acid type, and the sulfuric ester salt type; particularly preferable is the sulfuric ester salt type.

Specific examples include fatty acid soaps (for example, sodium laurate and sodium palmitate); higher alkyl sulfuric acid ester salts (for example, sodium lauryl sulfate and potassium lauryl sulfate); alkyl ether sulfuric acid ester salts (for example, POE-triethanolamine lauryl sulfate and sodium POE-lauryl sulfate); N-acyl sarcosinic acids (for example, sodium lauroyl sarcosinate); higher fatty acid amide sulfonic acid salts (for example, sodium N-myristoyl N-methyl taurate, sodium cocoyl methyl taurate, and sodium laurylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

A nonionic surfactant is a surfactant that is not ionized to assume an electric charge in an aqueous solution. For the hydrophobic group, a type that uses alkyls and a type that uses dimethyl silicone are known among others. Specific examples of the former include glycerol fatty acid esters, ethylene oxide derivatives of glycerol fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, and polyethylene glycol hydrogenated castor oil derivatives. Examples of the latter include polyether-modified silicone and polyglycerin-modified silicone. Preferable is the type that uses alkyl for the hydrophobic group.

Specific examples of the lipophilic nonionic surfactants include sorbitan fatty acid esters (for example, sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate); glycerin polyglycerin aliphatic acids (for example, mono cottonseed oil fatty acid glycerin, glyceryl monoerucate, glycerin sesquioleate, glyceryl monostearate, α,α'-glycerin oleate pyroglutamate, monostearate glycerin malic acid); propylene glycol fatty acid esters (for example, propylene glycol monostearate); hydrogenated castor oil derivatives; and glycerin alkylethers.

Examples of hydrophilic nonionic surfactants include POE-sorbitan fatty acid esters (for example, POE-sorbitan monooleate, POE-sorbitan monostearate, POE-sorbitan monooleate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); pluaronics (for example, pluaronic); POE• POP-alkylethers (for example, POE• POP-cetyl ether, POE• POP-2-decyl tetradecyl ether, POE• POP-monobutyl ether, POE• POP-lanolin hydrate, and POE• POP-glycerin ether); tetra POE• tetra POP-ethylenediamino condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax-lanolin derivatives (for example, POE-sorbitol beeswax); alkanol amides (for example, palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

Applications of the oil-in-water emulsified composition of the present invention are not limited; since it suppresses skin irritation and manifests superior texture, it can be preferably commercialized as skin cosmetics, hair cosmetics, external preparations, etc.

EXAMPLES

The present invention is described below by referring to Examples. The present invention is not limited to these Examples. First, Preparation examples of the copolymer (corona-core microgel) used in Examples are shown. The blend ratios are in wt % units unless specified otherwise.

<Preparation Example of the Copolymer (Corona-Core Microgel, Sometimes Simply Called "Microgel") Water Dispersion>

Polymerization of the corona-core microgel of the copolymer used in the present invention was conducted with the following method. PME-400, PME-1000, PME-4000, methyl methacrylate (MMA), butyl methacrylate (nBMA), 2-ethylhexyl methacrylate (EHMA), and ethylene glycol dimethacrylate (EGDMA) were dissolved into 100 ml of water-ethanol mixed solvent in a three-neck flask equipped with a reflux tube and a nitrogen feeding tube. After complete dissolution, 2,2'-azobis(2-methylpropionamidine)dihydrochloride in the amount of 1 mol % of the total amount of the monomer was added and dissolved. The completely homogenized polymerization solution was put through nitrogen substitution for 20 minutes to remove dissolved oxygen, followed by 8 hours of polymerization with stirring by means of a magnetic stirrer while the temperature was maintained at 65-70° C. in an oil bath. After completion of the polymerization, the polymerization solution was brought back to room temperature, and put through dialysis against water for five days to remove residual monomers and replace the dispersion fluid with water. The amounts of each monomer (g) are shown in Table 1 and the reaction conditions are shown in Table 2. In Table 1, all of Preparation examples 1-10 satisfy condition (A) and condition (B). Also, because of the aforementioned polymerization method, condition (D) is also satisfied in all of Preparation examples 1-10.

<Method for Measuring the Microgel Concentration in a Corona-Core Microgel Water Dispersion>

An appropriate amount of the water dispersion obtained with the method described above was weighed on an aluminum tray and dried one whole day at 90° C. Based on the weight values before and after the drying, the concentration of the corona-core microgel contained in the water dispersion was calculated.

TABLE 2

|  | (A) Macromonomer/ Hydrophobic monomer ratio (mole ratio) | (B) Feed amount of cross-linking monomer (wt %) | (C) Number of carbon atoms in hydrophobic monomer | (D) Water/ Ethanol solvent mix ratio (volume ratio) |
|---|---|---|---|---|
| Preparation example 1 | 1/100 | 0.5 | 1, 4 | 60/40 |
| Preparation example 2 | 1/100 | 0.3 | 1, 4 | 60/40 |
| Preparation example 3 | 1/100 | 1.0 | 1, 4 | 60/40 |
| Preparation example 4 | 1/100 | 0.5 | 1 | 70/30 |
| Preparation example 5 | 1/100 | 0.5 | 4 | 50/50 |
| Preparation example 6 | 1/100 | 0.5 | 8 | 40/60 |
| Preparation example 7 | 1/100 | 0.5 | 1, 4 | 60/40 |
| Preparation example 8 | 1/100 | 0.5 | 1, 4 | 60/40 |
| Preparation example 9 | 1/50 | 0.5 | 1, 4 | 70/30 |
| Preparation example 10 | 1/200 | 0.5 | 1, 4 | 50/50 |

<Method for Measuring the Particle Size>

The particle size of the microgel (copolymer) was measured using a Zetasizer from Malvern Instruments Ltd. A measurement sample was prepared for which the microgel concentration in the microgel dispersion was approximately 0.1 wt %; after removing debris with a 0.45 µm filter, the scattering strength at 25° C. was measured at a scattering angle of 90° and the average particle size was calculated with the analysis software installed on the measurement apparatus. The particle size was analyzed with the cumulant analysis method. For the viscosity of the solvent, which was necessary for the particle size analysis, the viscosity of pure water at 25° C., i.e., 0.89 mPas, was used.

TABLE 1

| | Macromonomer | | | Hydrophobic monomer | | | Cross-linking monomer |
|---|---|---|---|---|---|---|---|
| | PME-400 | PME-1000 | PME-4000 | MMA | n-BMA | EHMA | EGDMA |
| | Formula (1) | | | Formula (2) | | | Formula (3) |
| Preparation example 1 | | | 0.508 | 0.613 | 0.871 | | 0.007 |
| Preparation example 2 | | | 0.509 | 0.614 | 0.872 | | 0.004 |
| Preparation example 3 | | | 0.506 | 0.611 | 0.868 | | 0.015 |
| Preparation example 4 | | | 0.584 | 1.409 | | | 0.007 |
| Preparation example 5 | | | 0.450 | | 1.542 | | 0.008 |
| Preparation example 6 | | | 0.436 | | | 2.390 | 0.004 |
| Preparation example 7 | 0.086 | | | 0.787 | 1.117 | | 0.010 |
| Preparation example 8 | | 0.173 | | 0.751 | 1.067 | | 0.009 |
| Preparation example 9 | | | 0.811 | 0.489 | 0.694 | | 0.006 |
| Preparation example 10 | | | 0.291 | 0.703 | 0.998 | | 0.009 |

By conducting this measurement, it was possible to confirm synthesis of a microgel having a particle shape by the aforementioned preparation method.

<The Particle Size of Microgel and Concentration in the Water Dispersion>

The particle size and the concentration (wt %) in the water dispersion of the obtained microgel are shown in Table 3.

TABLE 3

|  | (nm) | (wt %) |
| --- | --- | --- |
| Preparation example 1 | 265 | 2.607 |
| Preparation example 2 | 242 | 1.729 |
| Preparation example 3 | 295 | 2.668 |
| Preparation example 4 | 290 | 2.273 |
| Preparation example 5 | 263 | 2.748 |
| Preparation example 6 | 258 | 2.686 |
| Preparation example 7 | 352 | 3.490 |
| Preparation example 8 | 292 | 2.945 |
| Preparation example 9 | 206 | 1.440 |
| Preparation example 10 | 648 | 2.132 |

Preparation examples and the evaluation method for the oil-in-water emulsified compositions evaluated in Examples are shown next. The blend ratios are in wt % units unless specified otherwise.

<Method for Preparing the Oil-in-Water Emulsified Composition>

Various water phase ingredients such as polyols and thickeners were added to purified water and mixed. Added to this was the microgel water dispersion, separately dispersed into purified water, obtained with the aforementioned preparation method, followed by stirring and mixing. However, when blending in a high concentration of the corona-core microgel or when it was difficult to blend in a necessary concentration of the microgel in water dispersion due to a high oil phase/water phase ratio, the microgel water dispersion obtained with the aforementioned preparation method was freeze-dried for one whole day to turn it into powder before blending it in. The microgel and the water phase ingredients were homogeneously dispersed, to which the oil phase ingredients were added, followed by shear mixing with a homomixer until homogeneous to obtain the oil-in-water emulsified composition.

The preparation method for Pickering emulsions using emulsification with a surfactant and those using powder ingredients that are not microgel is pursuant to the aforementioned technique unless described otherwise. That is, a surfactant or powder ingredients were dissolved or dispersed in the water phase, to which the oil phase ingredients were added, followed by shear mixing with a homomixer.

Evaluation (1): Emulsification Stability (Outer Appearance)

Within a day after the oil-in-water emulsified composition was prepared, the outer appearance of the oil-in-water emulsified composition was observed with the naked eye.

◯: The sample was homogeneous and no oil separation or aggregation was observed.

Δ: The sample was mostly homogeneous but slight oil separation was observed.

x: The sample was not homogeneous or significant oil separation or powder aggregation was observed.

Evaluation (2): Emulsification Stability (Emulsified Particles)

Emulsified particles of the sample were observed with an optical microscope.

◯: The sample was homogeneous and no coalescence or aggregation was observed.

Δ: The sample was mostly homogeneous but slight coalescence and/or aggregation was observed.

x: The sample was not homogeneous, or significant coalescence or powder aggregation was observed.

Evaluation (3): Skin Irritation Test

An occlusive patch was applied to the inner upper arm of ten panelists for 24 hours and the average value was calculated based on the following criteria.

0 - - - No abnormality was observed.
1 - - - Slight reddening was observed.
2 - - - Reddening was observed.
3 - - - Reddening and a papule were observed.

The evaluation criteria of the "skin irritation test" are as follows:

⊚: The average of the ten panelists is less than 0.15.
◯: The average of the ten panelists is 0.15 or more and less than 0.2.
Δ: The average of the ten panelists is 0.2 or more and less than 0.3.
x: The average of the ten panelists is 0.3 or more.

Evaluation (4): Evaluation of Dewy Freshness at the Time of Application

An actual use test for each sample was conducted by a panel of ten specialists. The evaluation criteria were as follows:

⊚: Eight or more panelists recognized dewy freshness during application.
◯: Six or more and less than eight panelists recognized dewy freshness during application.
Δ: Three or more and less than six panelists recognized dewy freshness during application.
x: Less than three panelists recognized dewy freshness during application.

Evaluation (5): Evaluation of Squeaky Sensation at the Time of Application

An actual use test for each sample was conducted by a panel of ten specialists. The evaluation criteria were as follows:

⊚: Eight or more panelists recognized there was no squeakiness during application.
◯: Six or more and less than eight panelists recognized there was no squeakiness during application.
Δ: Three or more and less than six panelists recognized there was no squeakiness during application.
x: Less than three panelists recognized there was no squeakiness during application.

Evaluation (6): Evaluation of Powdery Sensation at the Time of Application and after the Application An actual use test for each sample was conducted by a panel of ten specialists. The evaluation criteria were as follows:

⊚: Eight or more panelists recognized there was no powdery sensation during and after the application.
◯: Six or more and less than eight panelists recognized there was no powdery sensation during and after the application.
Δ: Three or more and less than six panelists recognized there was no powdery sensation during and after the application.
x: Less than three panelists recognized there was no powdery sensation during and after the application.

Evaluation (7): Stability Over Time

The emulsion of the water-in-oil emulsified composition was observed with the naked eye one month after preparation.

⊚: The composition was maintaining the emulsified state of the time of preparation.

◯: Some settling of the emulsified substance was seen but the composition mostly maintains the emulsified state.
Δ: The emulsified particles settled and coalescence of the particles was also observed.
x: The emulsified particles in the composition settled and coalesced, and the oil phase was completely separated.

The evaluation results of the oil-in-water emulsified compositions prepared with the aforementioned method are shown below. The microgel concentration in the table is a pure content concentration of the microgel original substance, regardless of whether the microgel used for the preparation was in the water dispersion form or a freeze-dried form. The pure content concentration when microgel water dispersion is blended in is calculated by using the microgel concentration value in the microgel dispersion shown in Table 3.

Blending in the Corona-Core Microgel Emulsifying Agent

Oil-in-water emulsified compositions having blend compositions described in the following Table 4 were prepared with the aforementioned method, and each sample was tested for the aforementioned evaluations (1)-(7).

TABLE 4

|  | Test example (%) | |
| --- | --- | --- |
|  | 1-1 | 1-2 |
| (a) Microgel of Preparation example 1 (pure content equivalent) | 1 | — |
| (b) Oil phase ingredients | | |
| Liquid petrolatum | 10 | 10 |
| Glyceryl tri-2-ethylhexanoate | 10 | 10 |
| Dimethylpolysiloxane (6 cs) | 10 | 10 |
| (c) Water phase ingredients | | |
| Ethanol | 5 | 5 |
| Dipropylene glycol | 5 | 5 |
| Carboxyvinyl polymer | 0.1 | 0.1 |
| Potassium hydroxide | 0.05 | 0.05 |
| Citric acid | 0.01 | 0.01 |
| Sodium citrate | 0.09 | 0.09 |
| Chelating agent | Appropriate amount | Appropriate amount |
| Ion-exchanged water | Balance | Balance |
| Evaluation (1): Emulsification stability (outer appearance) | ◯ | X |
| Evaluation (2): Emulsification stability (emulsified particles) | ◯ | X |
| Evaluation (3): Skin irritation | ◉ | ◯ |
| Evaluation (4): Dewy freshness | ◉ | X |
| Evaluation (5): Squeakiness | ◉ | ◉ |
| Evaluation (6): Powdery sensation | ◉ | ◉ |
| Evaluation (7): Stability over time | ◉ | X |

The results in Table 4 indicate that, in Test example 1-1 (Example of the present invention), the oil-in-water emulsified composition into which the microgel of Preparation example 1 was blended showed superior emulsification stability, low skin irritation, superior texture during use, and superior stability over time.

On the other hand, with the oil-in-water emulsified composition of Test example 1-2 (Comparative example of the present invention), oil-in-water emulsion is not formed to begin with and dewy fresh texture during use cannot be obtained.

That is, it is indicated that the microgel of Preparation example 1 functions as an emulsifying agent superior in terms of emulsification, stability, and texture during use in the oil-in-water emulsified composition of this composition.

Comparison with an Emulsified Composition Using a Surfactant

Next, in order to compare and evaluate the function of the microgel as an emulsifying agent with other commonly used surfactants, oil-in-water emulsions having blend compositions described in Table 5 were prepared with the aforementioned method and each sample was tested for the aforementioned evaluations (1)-(7).

TABLE 5

|  | Test example (%) | | |
| --- | --- | --- | --- |
|  | 2-1 | 2-2 | 2-3 |
| (a) Microgel of Preparation example 2 (pure content equivalent) | 1.2 | | |
| Polyoxyethylene (60) hydrogenated castor oil | | 1.2 | |
| Polyoxyethylene (60) sorbitan monostearate | | | 1.2 |
| (b) Oil phase ingredients | | | |
| Isoparaffin | 15 | 15 | 15 |
| Cetyl octanoate | 8 | 8 | 8 |
| Dimethylpolysiloxane (6 cs) | 12 | 12 | 12 |
| (c) Water phase ingredients | | | |
| Ethanol | 2 | 2 | 2 |
| Glycerin | 10 | 10 | 10 |
| Succinoglycan | 0.3 | 0.3 | 0.3 |
| Citric acid | 0.02 | 0.02 | 0.02 |
| Sodium citrate | 0.08 | 0.08 | 0.08 |
| Chelating agent | Appropriate amount | Appropriate amount | Appropriate amount |
| Ion-exchanged water | Balance | Balance | Balance |
| Evaluation (1): Emulsification stability (outer appearance) | ◯ | ◯ | ◯ |
| Evaluation (2): Emulsification stability (emulsified particles) | ◯ | ◯ | ◯ |
| Evaluation (3): Skin irritation | ◉ | ◯ | ◯ |
| Evaluation (4): Dewy freshness | ◉ | Δ | Δ |
| Evaluation (5): Squeakiness | ◉ | Δ | Δ |
| Evaluation (6): Powdery sensation | ◉ | ◉ | ◉ |
| Evaluation (7): Stability over time | ◉ | ◉ | ◉ |

The results in Table 5 indicate that, in Test example 2-1 (Example of the present invention), the oil-in-water emulsified composition into which the microgel of Preparation example 2 was blended showed superior emulsification stability, low skin irritation, superior texture during use, and superior stability over time.

On the other hand, the oil-in-water emulsified compositions of Test examples 2-2 and 2-3 (Comparative examples of the present invention), into which a surfactant was blended as an emulsifying agent, manifested superior emulsification stability and stability over time but lacked dewy freshness and gave a squeaky sensation, resulting in inferior texture during use. Also, some skin irritation was observed in Test example 2-3.

Comparison with an Emulsified Composition Using Powder

In order to compare and evaluate the function of the microgel as an emulsifying agent with conventional powder emulsification, oil-in-water emulsions having blend compositions described in Table 6 were prepared with the aforementioned method and each sample was tested for the aforementioned evaluations (1)-(7).

TABLE 6

| | Test example (%) | | |
|---|---|---|---|
| | 3-1 | 3-2 | 3-3 |
| (a) Microgel of Preparation example 2 (pure content equivalent) | 1 | | |
| Silica-coated zinc oxide | | 3 | |
| Dimethyl distearyl ammonium chloride | | 0.05 | |
| Hydrophobized silica | | | 3 |
| (b) Oil phase ingredients | | | |
| Decamethylcyclopentasiloxane | 8 | 8 | 8 |
| Isodecyl pivalate | 5 | 5 | 5 |
| Octylmethoxy cinnamate | 5 | 5 | 5 |
| (c) Water phase ingredients | | | |
| Ethanol | 2 | 2 | 2 |
| Glycerin | 5 | 5 | 5 |
| Succinoglycan | 0.35 | 0.35 | 0.35 |
| Citric acid | 0.01 | 0.01 | 0.01 |
| Sodium citrate | 0.09 | 0.09 | 0.09 |
| Chelating agent | Appropriate amount | Appropriate amount | Appropriate amount |
| Ion-exchanged water | Balance | Balance | Balance |
| Evaluation (1): Emulsification stability (outer appearance) | ○ | ○ | ○ |
| Evaluation (2): Emulsification stability (emulsified particles) | ○ | ○ | ○ |
| Evaluation (3): Skin irritation | ◎ | ◎ | ◎ |
| Evaluation (4): Dewy freshness | ◎ | ◎ | ◎ |
| Evaluation (5): Squeakiness | ◎ | Δ | Δ |
| Evaluation (6): Powdery sensation | ◎ | X | X |
| Evaluation (7): Stability over time | ◎ | ◎ | ◎ |

<Preparation Method for Test Example 3-2>

The water ingredients and silica-coated zinc oxide, which was the powder ingredient, were added to purified water and mixed. Stearyl trimethyl ammonium chloride or dimethyl distearyl ammonium chloride separately dispersed in purified water was added to this, followed by a heated ultrasonic treatment. After the powder ingredient was homogeneously dispersed, the rest of the oil phase ingredients were added, followed by mixing with a mixer until homogeneity was achieved to obtain an oil-in-water emulsion.

The results in Table 6 indicate that, in Test example 3-1 (Example of the present invention), the oil-in-water emulsified composition into which the microgel of Preparation example 2 was blended showed superior emulsification stability, low skin irritation, superior texture during use, and superior stability over time.

On the other hand, the oil-in-water emulsified compositions of Test example 3-2, into which silica-coated zinc oxide was blended as an emulsifying agent, and Test example 3-3, into which hydrophobized silica was blended, manifested superior emulsification stability, low skin irritation, and stability over time but the use of powder as the emulsifying agent and a high concentration required to obtain a stable oil-in-water emulsified composition caused a squeaky sensation and powdery sensation, resulting in inferior texture during use.

Investigating the Oil Phase Ingredients/Water Phase Ingredients Ratio

In order to evaluate the blend ratios of the oil phase ingredients and water phase ingredients of the oil-in-water emulsified composition using the microgel, oil-in-water emulsions having blend compositions described in Table 7 were prepared with the aforementioned method and each sample was tested for the aforementioned evaluations (1)-(7).

TABLE 7

| | Test example (%) | | | | | |
|---|---|---|---|---|---|---|
| | 4-1 | 4-2 | 4-3 | 4-4 | 4-5 | 4-6 |
| (a) Microgel of Preparation example 3 (pure content equivalent) | 1 | 1 | 1 | 1 | 1 | 1 |
| (b) Oil phase ingredients | | | | | | |
| Isododecane | 10 | 15 | 25 | 35 | 40 | 45 |
| Dimethylpolysiloxane (6 cs) | 10 | 15 | 25 | 35 | 40 | 45 |
| (c) Water phase ingredients | | | | | | |
| Ethanol | 2 | 2 | 2 | 2 | 2 | 2 |
| Carboxyvinyl polymer | 0.1 | 0.1 | 0.1 | 0.1 | 0.1 | 0.1 |
| Potassium hydroxide | 0.05 | 0.05 | 0.05 | 0.05 | 0.05 | 0.05 |
| Citric acid | 0.01 | 0.01 | 0.01 | 0.01 | 0.01 | 0.01 |
| Sodium citrate | 0.09 | 0.09 | 0.09 | 0.09 | 0.09 | 0.09 |
| Chelating agent | Appropriate amount | Appropriate amount | Appropriate amount | Appropriate amount | Appropriate amount | Appropriate amount |
| Ion-exchanged water | Balance | Balance | Balance | Balance | Balance | Balance |
| Oil phase ingredients/water phase ingredients ratio (mass ratio) | 20/80 | 30/70 | 50/50 | 70/30 | 80/20 | 90/10 |
| Evaluation (1): Emulsification stability (outer appearance) | ○ | ○ | ○ | ○ | ○ | ○ |
| Evaluation (2): Emulsification stability (emulsified particles) | ○ | ○ | ○ | ○ | ○ | Δ |
| Evaluation (3): Skin irritation | ◎ | ◎ | ◎ | ◎ | ◎ | ◎ |
| Evaluation (4): Dewy freshness | ◎ | ◎ | ◎ | ◎ | ◎ | ○ |
| Evaluation (5): Squeakiness | ◎ | ◎ | ◎ | ◎ | ◎ | ◎ |
| Evaluation (6): Powdery sensation | ◎ | ◎ | ◎ | ◎ | ◎ | ◎ |

TABLE 7-continued

|  | Test example (%) | | | | | |
| --- | --- | --- | --- | --- | --- | --- |
|  | 4-1 | 4-2 | 4-3 | 4-4 | 4-5 | 4-6 |
| Evaluation (7): Stability over time | ◎ | ◎ | ◎ | ◎ | ○ | Δ |

The results in Table 7 indicate that, in Test examples 4-1 through 4-6 (Examples of the present invention), emulsions with different oil phase ingredients/water phase ingredients ratios into which the microgel of Preparation example 3 was blended showed superior emulsification stability, low skin irritation, superior texture during use, and superior stability over time.

Test example 4-6, which had a very high oil component concentration, with an oil phase ingredients/water phase ingredients ratio of 90/10, resulted in some reduction in emulsification stability and stability over time; however, it has become clear that the copolymer (microgel) of the present invention can turn compositions having a very wide range of the oil phase ingredients/water phase ingredients ratio into a stable oil-in-water emulsified composition.

Blend Ratio of the Copolymer (Microgel)

In order to evaluate the blend ratios of the copolymer (microgel) of the oil-in-water emulsified composition of the present invention, oil-in-water emulsions of Test examples having blend compositions described in Table 8 were prepared with the aforementioned method and each sample was tested for the aforementioned evaluations (1)-(7).

The results in Table 8 indicate that, in Test examples 5-1 through 5-5 (Examples of the present invention), emulsions with different microgel blend ratios of Preparation example 4 showed superior emulsification stability, low skin irritation, superior texture during use, and superior stability over time.

On the other hand, Test example 5-6 (Example of the present invention) having a very low concentration of Preparation example 4 of 0.05% showed some reduction in emulsification stability and stability over time. Also, Test example 5-1, although the texture during use was superior, had a tendency to give some squeakiness and/or powdery sensation, perhaps due to a high microgel blend ratio of 5%.

Evaluation of the Composition of the Copolymer (Microgel)

In order to evaluate the composition of the copolymer (corona-core microgel) in the oil-in-water emulsified composition of the present invention, copolymers (microgel) described in Table 9 and Table 10 were prepared. The preparation method and the particle size measurement method are pursuant to the aforementioned methods.

TABLE 8

|  | Test example (%) | | | | | |
| --- | --- | --- | --- | --- | --- | --- |
|  | 5-1 | 5-2 | 5-3 | 5-4 | 5-5 | 5-6 |
| (a) Microgel of Preparation example 4 (pure content equivalent) | 5 | 3 | 1.5 | 0.5 | 0.1 | 0.05 |
| (b) Oil phase ingredients | | | | | | |
| Squalane | 12 | 12 | 12 | 12 | 12 | 12 |
| Pentaerythritol tetra-2 ethylhexanoate | 8 | 8 | 8 | 8 | 8 | 8 |
| Methylphenylpolysiloxane | 10 | 10 | 10 | 10 | 10 | 10 |
| (c) Water phase ingredients | | | | | | |
| Ethanol | 2 | 2 | 2 | 2 | 2 | 2 |
| 1,3-butylene glycol | 5 | 5 | 5 | 5 | 5 | 5 |
| Sodium hyaluronate | 0.05 | 0.05 | 0.05 | 0.05 | 0.05 | 0.05 |
| Polyoxyethylene decyltetradecyl ether/hexamethylene diisocyanate/polyethylene glycol 11000 copolymer | 0.1 | 0.1 | 0.1 | 0.1 | 0.1 | 0.1 |
| Citric acid | 0.01 | 0.01 | 0.01 | 0.01 | 0.01 | 0.01 |
| Sodium citrate | 0.09 | 0.09 | 0.09 | 0.09 | 0.09 | 0.09 |
| Chelating agent | Appropriate amount | Appropriate amount | Appropriate amount | Appropriate amount | Appropriate amount | Appropriate amount |
| Ion-exchanged water | Balance | Balance | Balance | Balance | Balance | Balance |
| Evaluation (1): Emulsification stability (outer appearance) | ○ | ○ | ○ | ○ | ○ | Δ |
| Evaluation (2): Emulsification stability (emulsified particles) | ○ | ○ | ○ | ○ | ○ | Δ |
| Evaluation (3): Skin irritation | ◎ | ◎ | ◎ | ◎ | ◎ | ◎ |
| Evaluation (4): Dewy freshness | ◎ | ◎ | ◎ | ◎ | ◎ | ◎ |
| Evaluation (5): Squeakiness | ○ | ◎ | ◎ | ◎ | ◎ | ◎ |
| Evaluation (6): Powdery sensation | ○ | ◎ | ◎ | ◎ | ◎ | ◎ |
| Evaluation (7): Stability over time | ◎ | ◎ | ◎ | ◎ | ○ | Δ |

TABLE 9

|  | Macromonomer | | Hydrophobic monomer | | | Crosslinking agent EGDMA | Particle size |
| --- | --- | --- | --- | --- | --- | --- | --- |
|  | PME-200 | PME-4000 | MMA | n-BMA | Dodecyl methacrylate | | |
| Comparative preparation example 1 | 0.056 |  | 0.799 | 1.135 |  | 0.010 | 637 |
| Comparative preparation example 2 |  | 0.503 | 0.606 | 0.861 |  | 0.029 | 480 |
| Comparative preparation example 3 |  | 0.510 | 0.615 | 0.874 |  | 0.001 | 256 |
| Comparative preparation example 4 |  | 0.204 | 0.738 | 1.049 |  | 0.009 | Unable to measure |
| Comparative preparation example 5 |  | 1.620 | 0.156 | 0.222 |  | 0.002 | Unable to measure |

TABLE 10

| | (A) Macromonomer/Hydrophobic monomer ratio (mole ratio) | (B) Feed amount of the cross-linking monomer (wt %) | (C) Number of carbon atoms in hydrophobic monomer | (D) Water/Ethanol solvent mix ratio (volume ratio) |
| --- | --- | --- | --- | --- |
| Comparative preparation example 1 | 1/100 | 0.5 | 1, 4 | 60/40 |
| Comparative preparation example 2 | 1/100 | 2 | 1, 4 | 60/40 |
| Comparative preparation example 3 | 1/100 | 0.05 | 1, 4 | 60/40 |
| Comparative preparation example 4 | 1/300 | 0.5 | 1, 4 | 30/70 |
| Comparative preparation example 5 | 1/8 | 0.5 | 1, 4 | 70/30 |

Evaluation of the Composition of the Copolymer (Microgel)

(1) Chain Length of the Macromonomer

In order to evaluate the macromonomer composition of the copolymer (microgel) structure of the oil-in-water emulsified composition of the present invention, oil-in-water emulsions of Test examples having blend compositions described in Table 11 were prepared with the aforementioned method and each sample was tested for the aforementioned evaluations (1)-(7).

TABLE 11

| | Test example (%) | | | | | | | |
| --- | --- | --- | --- | --- | --- | --- | --- | --- |
| | 6-1 | 6-2 | 6-3 | 6-4 | 6-5 | 6-6 | 6-7 | 6-8 |
| Microgel of Comparative preparation example 1 (pure content equivalent) | 1 | 1 | | | | | | |
| (a) Microgel of Preparation example 7 (pure content equivalent) | | | 1 | 1 | | | | |
| (a) Microgel of Preparation example 8 (pure content equivalent) | | | | | 1 | 1 | | |
| (a) Microgel of Preparation example 1 (pure content equivalent) | | | | | | | 1 | 1 |
| (b) Oil phase ingredients | | | | | | | | |
| Liquid petrolatum | 15 | 30 | 15 | 30 | 15 | 30 | 15 | 30 |
| Isopropyl myristate | 10 | 20 | 10 | 20 | 10 | 20 | 10 | 20 |
| Methylphenylpolysiloxane | 5 | 10 | 5 | 10 | 5 | 10 | 5 | 10 |
| (c) Water phase ingredients | | | | | | | | |
| Ethanol | 3 | 3 | 3 | 3 | 3 | 3 | 3 | 3 |
| 1,3-butylene glycol | 5 | 5 | 5 | 5 | 5 | 5 | 5 | 5 |
| Carboxyvinyl polymer | 0.15 | 0.15 | 0.15 | 0.15 | 0.15 | 0.15 | 0.15 | 0.15 |
| Potassium hydroxide | 0.08 | 0.08 | 0.08 | 0.08 | 0.08 | 0.08 | 0.08 | 0.08 |
| Citric acid | 0.02 | 0.02 | 0.02 | 0.02 | 0.02 | 0.02 | 0.02 | 0.02 |
| Sodium citrate | 0.08 | 0.08 | 0.08 | 0.08 | 0.08 | 0.08 | 0.08 | 0.08 |

TABLE 11-continued

|  | Test example (%) | | | | | | | |
|---|---|---|---|---|---|---|---|---|
|  | 6-1 | 6-2 | 6-3 | 6-4 | 6-5 | 6-6 | 6-7 | 6-8 |
| Chelating agent | Appropriate amount | Appropriate amount | Appropriate amount | Appropriate amount | Appropriate amount | Appropriate amount | Appropriate amount | Appropriate amount |
| Ion-exchanged water | Balance | Balance | Balance | Balance | Balance | Balance | Balance | Balance |
| Molecular weight of macromonomer PEG | 200 | 200 | 400 | 400 | 1000 | 1000 | 4000 | 4000 |
| Evaluation (1): Emulsification stability (outer appearance) | ○ | X | ○ | ○ | ○ | ○ | ○ | ○ |
| Evaluation (2): Emulsification stability (Emulsified particles) | Δ | X | ○ | Δ | ○ | ○ | ○ | ○ |
| Evaluation (3): Skin irritation | ◎ | — | ◎ | ◎ | ◎ | ◎ | ◎ | ◎ |
| Evaluation (4): Dewy freshness | ◎ | — | ◎ | ◎ | ◎ | ◎ | ◎ | ◎ |
| Evaluation (5): Squeakiness | ◎ | — | ◎ | ◎ | ◎ | ◎ | ◎ | ◎ |
| Evaluation (6): Powdery sensation | ◎ | — | ◎ | ◎ | ◎ | ◎ | ◎ | ◎ |
| Evaluation (7): Stability over time | Δ | — | ◎ | ○ | ◎ | ◎ | ◎ | ◎ |

The results in Table 11 indicate that, in Test examples 6-3 through 6-8 (Examples of the present invention), all the emulsions into which microgels having different chain lengths were blended showed superior emulsification stability, low skin irritation, superior texture during use, and superior stability over time. In Test examples 6-1 and 6-2 (Comparative examples of the present invention), into which the microgel of Comparative preparation example 1 prepared with the macromonomer having a short polyoxyethylene chain length (polyoxyethylene part molecular weight: approximately 200) was blended, the emulsification stability was low, and Test example 6-2, which had a higher oil phase blend ratio, did not even provide a stable emulsified composition.

Evaluation of the Composition of the Copolymer (Microgel) (2) Cross-Link Density In order to evaluate the cross-link density of the copolymer (corona-core microgel) structure of the oil-in-water emulsified composition of the present invention, oil-in-water emulsions of Test examples having blend compositions described in Table 12 were prepared with the aforementioned method and each sample was tested for the aforementioned evaluations (1)-(7).

TABLE 12

|  | Test example (%) | | | | |
|---|---|---|---|---|---|
|  | 7-1 | 7-2 | 7-3 | 7-4 | 7-5 |
| (a) Microgel of Preparation example 1 (pure content equivalent) | 1 | | | | |
| (a) Microgel of Preparation example 2 (pure content equivalent) | | 1 | | | |
| (a) Microgel of Preparation example 3 (pure content equivalent) | | | 1 | | |
| (a) Microgel of Comparative preparation example 2 (pure content equivalent) | | | | 1 | |
| (a) Microgel of Comparative preparation example 3 (pure content equivalent) | | | | | 1 |
| (b) Oil phase ingredients | | | | | |
| Isoparaffin | 20 | 20 | 20 | 20 | 20 |
| Tripropylene glycol pivalate | 5 | 5 | 5 | 5 | 5 |
| Octylmethoxy cinnamate | 5 | 5 | 5 | 5 | 5 |
| (c) Water phase ingredients | | | | | |
| Ethanol | 2 | 2 | 2 | 2 | 2 |
| Dipropylene glycol | 5 | 5 | 5 | 5 | 5 |
| Carboxyvinyl polymer | 0.15 | 0.15 | 0.15 | 0.15 | 0.15 |
| Potassium hydroxide | 0.08 | 0.08 | 0.08 | 0.08 | 0.08 |
| Citric acid | 0.02 | 0.02 | 0.02 | 0.02 | 0.02 |
| Sodium citrate | 0.08 | 0.08 | 0.08 | 0.08 | 0.08 |
| Chelating agent | Appropriate amount | Appropriate amount | Appropriate amount | Appropriate amount | Appropriate amount |
| Ion-exchanged water | Balance | Balance | Balance | Balance | Balance |
| Cross-link density (wt %) | 0.5 | 0.3 | 1.0 | 2 | 0.05 |
| Evaluation (1): Emulsification stability (outer appearance) | ○ | ○ | ○ | ○ | ○ |

TABLE 12-continued

|  | Test example (%) | | | | |
| --- | --- | --- | --- | --- | --- |
|  | 7-1 | 7-2 | 7-3 | 7-4 | 7-5 |
| Evaluation (2): Emulsification stability (emulsified particles) | ○ | ○ | ○ | Δ | X |
| Evaluation (3): Skin irritation | ⊚ | ⊚ | ⊚ | ⊚ | ⊚ |
| Evaluation (4): Dewy freshness | ⊚ | ⊚ | ⊚ | ⊚ | ⊚ |
| Evaluation (5): Squeakiness | ⊚ | ⊚ | ⊚ | ○ | ⊚ |
| Evaluation (6): Powdery sensation | ⊚ | ⊚ | ⊚ | Δ | ⊚ |
| Evaluation (7): Stability over time | ⊚ | ⊚ | ⊚ | Δ | X |

The results in Table 12 indicate that, in Test examples 7-1 through 7-3 (Examples of the present invention), all the emulsions into which microgels having different cross-link density were blended showed superior emulsification stability, low skin irritation, superior texture during use, and superior stability over time. Test example 7-4 (Comparative example of the present invention), into which the microgel of Comparative preparation example 2 having a high cross-link density was blended, showed low emulsification stability and somewhat inferior texture during use. Test example 7-5 (Comparative example of the present invention), into which the microgel of Comparative preparation example 3 having a low cross-link density was blended, showed superior texture during use but had a tendency for very low emulsification stability.

Evaluation of the Composition of the Copolymer (Microgel)
(3) Macromonomer/Hydrophobic Monomer Ratio In order to evaluate the macromonomer/hydrophobic monomer ratio of the copolymer (microgel) structure of the oil-in-water emulsified composition of the present invention, oil-in-water emulsions of Test examples having blend compositions described in Table 13 were prepared with the aforementioned method and each sample was tested for the aforementioned evaluations (1)-(7).

TABLE 13

|  | Test example (%) | | | | |
| --- | --- | --- | --- | --- | --- |
|  | 8-1 | 8-2 | 8-3 | 8-4 | 8-5 |
| (a) Microgel of Preparation example 1 (pure content equivalent) | 1 | | | | |
| (a) Microgel of Preparation example 9 (pure content equivalent) | | 1 | | | |
| (a) Microgel of Preparation example 10 (pure content equivalent) | | | 1 | | |
| (a) Microgel of Comparative preparation example 4 (pure content equivalent) | | | | 1 | |
| (a) Microgel of Comparative preparation example 5 (pure content equivalent) | | | | | 1 |
| (b) Oil phase ingredients | | | | | |
| Isoparaffin | 20 | 20 | 20 | 20 | 20 |
| Tripropylene glycol pivalate | 5 | 5 | 5 | 5 | 5 |
| Octylmethoxy cinnamate | 5 | 5 | 5 | 5 | 5 |
| (c) Water phase ingredients | | | | | |
| Ethanol | 2 | 2 | 2 | 2 | 2 |
| Dipropylene glycol | 5 | 5 | 5 | 5 | 5 |
| Succinoglycan | 0.35 | 0.35 | 0.35 | 0.35 | 0.35 |
| Citric acid | 0.02 | 0.02 | 0.02 | 0.02 | 0.02 |
| Sodium citrate | 0.08 | 0.08 | 0.08 | 0.08 | 0.08 |
| Chelating agent | Appropriate amount | Appropriate amount | Appropriate amount | Appropriate amount | Appropriate amount |
| Ion-exchanged water | Balance | Balance | Balance | Balance | Balance |
| Macromonomer/hydrophobic monomer ratio | 1/100 | 1/50 | 1/200 | 1/300 | 1/8 |
| Evaluation (1): Emulsification stability (outer appearance) | ○ | ○ | ○ | X | Δ |
| Evaluation (2): Emulsification stability (emulsified particles) | ○ | ○ | Δ | — | X |
| Evaluation (3): Skin irritation | ⊚ | ⊚ | ⊚ | — | ⊚ |
| Evaluation (4): Dewy freshness | ⊚ | ⊚ | ⊚ | — | ⊚ |
| Evaluation (5): Squeakiness | ⊚ | ⊚ | ⊚ | — | ⊚ |
| Evaluation (6): Powdery sensation | ⊚ | ⊚ | ⊚ | — | ⊚ |
| Evaluation (7): Stability over time | ⊚ | ⊚ | ○ | — | X |

The results in Table 13 indicate that, in Test examples 8-1 through 8-3 (Examples of the present invention), all the emulsions into which microgels having different macromonomer/hydrophobic monomer ratios were blended showed superior emulsification stability, low skin irritation, superior texture during use, and superior stability over time. The microgel of Comparative preparation example 4, which had a high hydrophobic monomer ratio, did not even result in a good microgel preparation and Test Example 8-4 (Comparative example of the present invention), into which it was blended, also failed to form an oil-in-water emulsion. The microgel of Comparative preparation example 5, which had a low hydrophobic monomer ratio, also did not even result in a good microgel preparation and Test Example 8-5 (Comparative example of the present invention), into which it was blended, also showed a tendency for low emulsification stability.

Evaluation (8): Durability of Fragrance

A prescribed amount of the sample was applied on the skin and a panel of specialists evaluated the magnitude of the fragrance after one hour.

◉: Strong
○: Somewhat strong
Δ: Neither strong nor weak (normal level)
x: Weak water emulsified composition into which the microgel of Preparation example 1 was blended showed superior emulsification stability, low skin irritation, superior texture during use, superior stability over time, and durability of fragrance.

On the other hand, in Text example 9-5 (Comparative example of the present invention), into which polyoxyethylene (60) hydrogenated castor oil, a surfactant, was blended as an emulsifying agent, it was not possible to obtain a base agent having emulsified perfume ingredients, the base agent stability and texture during use were inferior, and durability of fragrance was not observed. Also, in Test example 9-5 (Comparative example of the present invention), which contained hydrophobized silica as the emulsifying agent and had a total of 10% of perfume ingredients, the emulsified base agent was obtained but stability over time was inferior. Powdery sensation and/or squeakiness due to the powder was also sensed. Furthermore, in Test example 9-6 (Comparative example of the present invention), which had a total of 20% of perfume ingredients, it was not even possible to obtain a base agent into which the perfume ingredients were emulsified. Furthermore, in both Test example 9-6 and Test Example 9-7 (Comparative examples of the present invention), durability of fragrance was not observed.

The following are formulation examples of various cosmetics into which the oil-in-water emulsified compositions of the present invention are blended; the present invention is not limited to these. All of the cosmetics obtained from the

TABLE 14

| | | Test example (%) | | | | | | |
|---|---|---|---|---|---|---|---|---|
| | | 9-1 | 9-2 | 9-3 | 9-4 | 9-5 | 9-6 | 9-7 |
| Corona-core microgel emulsifying agent | (a) Microgel of Preparation example 1 (pure content equivalent) | 1 | 1 | 1 | 1 | | | |
| Emulsifier | Polyoxyethylene (60) hydrogenated castor oil | | | | | 1 | | |
| Powder (Emulsifying agent) | Hydrophobized silica | | | | | | 1 | 1 |
| Oil phase ingredients (Perfume) | (b) Limonene | 5 | 10 | 15 | 20 | 5 | 10 | 15 |
| | (b) Citral | 5 | 10 | 15 | 20 | 5 | 10 | 15 |
| Water phase ingredients | (c) Ion exchanged water | Balance | Balance | Balance | Balance | Balance | Balance | Balance |
| Evaluation (1): Emulsification stability (outer appearance) | | ○ | ○ | ○ | ○ | X | ○ | X |
| Evaluation (2): Emulsification stability (Emulsified particles) | | ○ | ○ | ○ | ○ | X | ○ | X |
| Evaluation (3): Skin irritation | | ◉ | ◉ | ○ | ○ | ○ | ◉ | ◉ |
| Evaluation (4): Dewy freshness | | ◉ | ◉ | ◉ | ○ | X | ○ | ○ |
| Evaluation (5): Squeakiness | | ◉ | ◉ | ◉ | ◉ | ◉ | Δ | Δ |
| Evaluation (6): Powdery sensation | | ◉ | ◉ | ◉ | ◉ | ◉ | X | X |
| Evaluation (7): Stability over time | | ◉ | ◉ | ◉ | ◉ | X | ◉ | X |
| Evaluation (8): Durability of fragrance | | ○ | ○ | ◉ | ◉ | X | Δ | Δ |

The results in Table 14 indicate that, in Test examples 9-1 through 9-4 (Examples of the present invention), the oil-infollowing formulation examples manifested a high emulsification stability, low skin irritation, and superior texture during use. The microgel blend ratios in Examples are in pure content equivalent units.

Example 1

Emulsion

| | |
|---|---|
| Microgel of Preparation example 1 | 1 |
| Dimethylpolysiloxane (6 cs) | 3 |
| Decamethylcyclopentasiloxane | 4 |
| Ethanol | 5 |
| Glycerin | 6 |
| 1,3-Butylene glycol | 5 |
| Polyoxyethylene methyl glucoside | 3 |
| Sunflower oil | 1 |
| Squalane | 2 |
| Potassium hydroxide | 0.1 |
| Sodium hexametaphosphate | 0.05 |
| Hydroxypropyl-β-cyclodextrin | 0.1 |
| Dipotassium glycyrrhizinate | 0.05 |
| Loquat leaf extract | 0.1 |
| Sodium L-glutamate | 0.05 |
| Fennel extract | 0.1 |
| Yeast extract | 0.1 |
| Lavender oil | 0.1 |
| Rehmannia extract | 0.1 |
| Dimorpholinopyridazinone | 0.1 |
| Xanthan gum | 0.1 |
| Carboxyvinyl polymer | 0.1 |
| Red iron oxide | Appropriate amount |
| Yellow iron oxide | Appropriate amount |
| Paraben | Appropriate amount |
| Purifiedwater | Balance |

Example 2

Moisturizing Cream

| | |
|---|---|
| Microgel of Preparation example 3 | 1.5 |
| Liquid paraffin | 10 |
| Dimethylpolysiloxane (6 cs) | 5 |
| Squalane | 15 |
| Pentaerythritol tetra-2-ethylhexanoate | 5 |
| Glycerin tri-2-ethylhexanoate | 10 |
| Glycerin | 10 |
| 1,3-Butylene glycol | 2 |
| Erythritol | 1 |
| Polyethylene glycol 1500 | 5 |
| Potassium hydroxide | 0.1 |
| Sodium hexametaphosphate | 0.05 |
| Tocopherol acetate | 0.05 |
| Paraoxybenzoic ester | Appropriate amount |
| Hydroxypropyl methylcellulose | 0.3 |
| Polyvinyl alcohol | 0.1 |
| Carboxyvinyl polymer | 0.2 |
| Purified water | Balance |

Example 3

Cleansing Cream

| | |
|---|---|
| Microgel of Preparation example 5 | 1.5 |
| α-Olefin oligomer | 20 |
| Petrolatum | 5 |
| Glyceryl tri-2-ethylhexanoate | 20 |
| Dimethylpolysiloxane (6 cs) | 2 |
| Methylphenylpolysiloxane | 15 |
| Batyl alcohol | 0.5 |
| Polyoxyethylene/methylpolysiloxane copolymer | 1 |
| Glycerin | 7 |
| Sorbit solution (70%) | 18 |
| Polyoxyethylene (60) hydrogenated castor oil | 1 |
| Polyoxyethylene (25) polyoxypropylene glycol (30) | 2 |
| Sodium methyl cocoyl taurate | 1 |
| L-Serine | 0.1 |
| Phellodendri Cortex extract | 0.1 |
| Sodium alginate | 0.1 |
| Purified water | Balance |
| Perfume | Appropriate amount |

Example 4

Sunscreen Emulsion

| | |
|---|---|
| Microgel of Preparation example 6 | 1.2 |
| Isododecane | 8 |
| Octyl octanoate | 5 |
| Ethylhexyl methoxycinnamate | 5 |
| Octocrylene | 2 |
| Bis-ethylhexyloxyphenol methoxyphenyl triazine | 3 |
| Oxybenzone | 1 |
| Ethanol | 5 |
| 1,3-Butylene glycol | 5 |
| Triethanolamine | 0.1 |
| Xanthan gum | 0.1 |
| (Acrylic acid/alkyl acrylate (C10-30)) copolymer | 0.1 |
| Carbomer | 0.1 |
| Tranexamic acid | 2 |
| Talc | 3 |
| Phenoxyethanol | Appropriate amount |
| Disodium edetate | Appropriate amount |
| Purified water | Balance |
| Perfume | Appropriate amount |

Example 5

Cleansing Lotion

| | |
|---|---|
| Microgel of Preparation example 7 | 1 |
| Liquid paraffin | 10 |
| Petrolatum | 5 |
| Cetanol | 1 |
| Diglycerin | 0.5 |
| 1,3-Butylene glycol | 5 |
| Polyethylene glycol 1500 | 3 |
| Stearic acid | 2 |
| Polyoxyethylenesorbitan monolaurate (20 E.O.) | 0.2 |
| Triethanolamine | 1 |
| Tocopherol acetate | 0.1 |
| Carboxyvinyl polymer | 0.03 |
| Paraben | Appropriate amount |
| Purified water | Balance |

Example 6

Hair Cream

| | |
|---|---|
| Microgel of Preparation example 8 | 0.8 |
| Liquid paraffin | 5 |
| Petrolatum | 2 |
| Dimethylpolysiloxane (6 cs) | 5 |
| Cetanol | 4 |
| Stearyl alcohol | 1 |
| 1,3-Butylene glycol | 10 |
| Polyoxypropylene glyceryl ether | 2 |
| Lipophilic glycerin monostearate | 2 |
| Polymer JR-400 | 0.5 |
| Paraoxybenzoic ester | Appropriate amount |
| Purified water | Balance |
| Perfume | Appropriate amount |

Example 7

Hair Styling Cream

| | |
|---|---|
| Microgel of Preparation example 1 | 1.1 |
| Volatile isoparaffin | 5 |
| Dimethylpolysiloxane (6 cs) | 2 |
| High polymerization methylpolysiloxane | 2 |
| Ethanol | 5 |
| Glycerin | 5 |
| Polyoxypropylene decaglyceryl ether | 5 |
| Isostearic acid | 1 |
| Sodium hydroxide | 0.15 |
| Paraoxybenzoic ester | Appropriate amount |
| Phenoxyethanol | Appropriate amount |
| Trisodium edetate | Appropriate amount |
| Xanthan gum | 0.5 |
| Carrageenan | 0.3 |
| Vinyl acetate/vinyl pyrrolidone copolymer | 2 |
| Carboxyvinyl polymer | 0.5 |
| Purified water | Balance |

Example 8

Hair Oil Cream

| | |
|---|---|
| Microgel of Preparation example 2 | 2 |
| Hydrogenated polyisobutene | Balance |
| Ethanol | 10 |
| Oxybenzone | Appropriate amount |
| High polymerization methylpolysiloxane | 10 |

Example 9

Hair Treatment

| | |
|---|---|
| Microgel of Preparation example 5 | 1.2 |
| Dimethylpolysiloxane (6 cs) | 2 |
| Cetanol | 0.5 |
| Behenyl alcohol | 3 |
| Glycerin | 3 |
| Cetyl 2-ethylhexanoate | 1 |
| Stearyltrimethylammonium chloride | 0.7 |
| Citric acid | 0.05 |
| Sodium lactate solution | 0.01 |
| Dipotassium glycyrrhizinate | 0.1 |
| Lily extract | 0.1 |
| Hydroxyethyl cellulose | 0.1 |
| Paraoxybenzoic ester | Appropriate amount |
| Purified water | Balance |
| Perfume | Appropriate amount |

Example 10

Emulsified Foundation

| | |
|---|---|
| Microgel of Preparation example 2 | 2.5 |
| Alkyl-modified silicone resin-coated titanium dioxide | 9.0 |
| Alkyl-modified silicone resin-coated fine particle titanium dioxide (40 nm) | 5.0 |
| Alkyl-modified silicone resin-coated iron oxide (red) | 0.5 |
| Alkyl-modified silicone resin-coated iron oxide (yellow) | 1.5 |
| Alkyl-modified silicone resin-coated iron oxide (black) | 0.2 |
| Polyoxyalkylene-modified organopolysiloxane | 0.5 |
| Decamethylpentacyclosiloxane | 5.0 |
| Octyl paramethoxycinnamate | 5.0 |
| Acryl silicone | 4.0 |
| Dynamite glycerin | 6.0 |
| Xanthan gum | 0.1 |
| Carboxymethyl cellulose | 0.3 |
| Sodium acryloyldimethyltaurate/hydroxyethyl acrylate copolymer (Content: 35-40 wt %) | 1.5 |
| Ethanol | 5.0 |
| Ion-exchanged water | Balance |

Formulation Example 1

Floral Blend Perfume B

| | |
|---|---|
| Orange oil | 4 |
| Lemon oil | 3 |
| Dihydromyrcenol | 3 |
| Linarol | 15 |
| Rose base | 12 |
| Terpineol | 5 |
| Methyl ionone gamma | 5 |
| Beta ionone | 5 |
| Vertofix | 10 |
| Hedione | 18 |
| Florosa (from Quest International) | 20 |

Example 11

Water-Based Fragrance

| Ingredients | (wt %) |
|---|---|
| Microgel of Preparation example 2 (pure content) | 1.5 |
| Floral blend perfume B of the aforementioned Formulation example 1 | 20 |
| Dimethylpolysiloxane (6 cs) | 10 |
| Methylphenylpolysiloxane | 1 |

-continued

| Ingredients | (wt %) |
|---|---|
| Glycerin | 4 |
| Ethanol | 10 |
| Citric acid | 0.01 |
| Sodium citrate | 0.09 |
| Paraoxybenzoic ester | Appropriate amount |
| Ion-exchanged water | Balance |

INDUSTRIAL APPLICABILITY

According to the present invention, an oil-in-water emulsified composition superior in terms of emulsification stability and texture during use can be obtained by using a corona-core microgel as the emulsifying agent. The oil-in-water emulsified composition of the present invention has superior texture and therefore it is useful particularly for cosmetics.

The invention claimed is:

1. An oil-in-water Pickering emulsion comprising: a corona-core microgel emulsifying agent in an amount of 0.1-10 wt % of the total amount of the oil-in-water Pickering emulsion; an oil phase ingredient in an amount of 10-80 wt % of the total amount of the oil-in-water Pickering emulsion; and a water phase ingredient; wherein
the oil-in-water Pickering emulsion is formed by applying shearing force to a mixture of the corona-core microgel emulsifying agent, the oil phase ingredient, and the water phase ingredient;
the corona-core microgel emulsifying agent is adsorbed onto oil drops of the oil phase ingredient dispersed in the water phase ingredient; and
the corona-core microgel emulsifying agent is composed of a copolymer obtained by polymerizing polyethylene oxide macromonomers of the following formula (1), hydrophobic monomers of the following formula (2), and cross-linking monomers of the following formula (3) under the following conditions (A) and (B), and has a cross-link density of 0.5-100 wt %:
(A) a mole ratio of a feed mole amount of said polyethylene oxide macromonomers/a feed mole amount of the hydrophobic monomers is 1:10-1:250; and
(B) a feed amount of said cross-linking monomers is 0.1-1.5 wt % relative to a feed amount of said hydrophobic monomers;

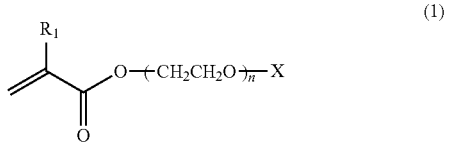
(1)

$R_1$ denotes an alkyl having 1-3 carbon atoms, n is an integer 8-200, and X denotes H or $CH_3$;

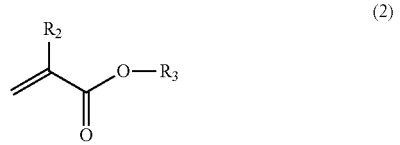
(2)

$R_2$ denotes an alkyl having 1-3 carbon atoms, and $R_3$ denotes an alkyl having 1-12 carbon atoms; and

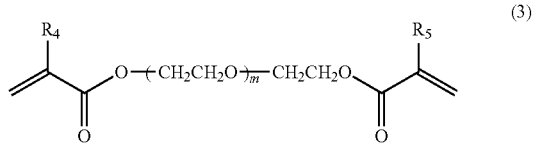
(3)

$R_4$ and $R_5$ each independently denote an alkyl having 1-3 carbon atoms, and m is a number 0-2.

2. The oil-in-water Pickering, emulsion of claim 1 wherein the following conditions (C) and (D) are added for radical polymerization of polyethylene oxide macromonomers of the following formula (1), hydrophobic monomers of the following formula (2), and cross-linking monomers of the following formula (3) in a water-ethanol mixed solvent to obtain the copolymer constituting the corona-core microgel emulsifying agent of claim 1;
(C) the hydrophobic monomers of the following formula (2) have a monomer composition of a mixture of one, two, or more methacrylic acid derivatives that have an alkyl having 1-8 carbon atoms; and
(D) the water-ethanol mixed solvent has a volume ratio at 20° C. of water:ethanol=90-30:10-70;

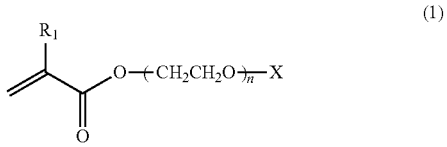
(1)

$R_1$ denotes an alkyl having 1-3 carbon atoms, n is an integer 8-200, and X denotes H or $CH_3$;

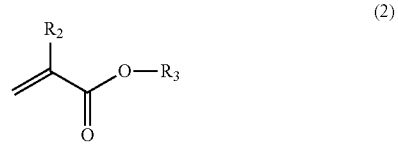
(2)

$R_2$ denotes an alkyl having 1-3 carbon atoms, and R denotes an alkyl having 1-12 carbon atoms; and

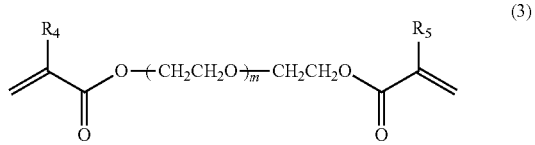
(3)

$R_4$ and $R_5$ each independently denote an alkyl having 1-3 carbon atoms, and m is a number 0-2.

3. The oil-in-water Pickering emulsion of claim 1 comprising perfume as the oil phase ingredient in an amount of 0.5-40 wt % of the total amount of the oil-in-water Pickering emulsion.

4. The oil-in-water Pickering emulsion of claim 2 comprising perfume as the oil phase ingredient in an amount of 0.5-40 wt % of the total amount of the oil-in-water Pickering emulsion.

* * * * *